(12) United States Patent
Mehmet

(10) Patent No.: US 11,024,412 B2
(45) Date of Patent: *Jun. 1, 2021

(54) METHOD FOR PREPARING A CUSTOMIZED EXERCISE STRATEGY

(71) Applicant: Tansu Mehmet, Pristina Kosova (RS)

(72) Inventor: Tansu Mehmet, Pristina Kosova (RS)

(*) Notice: Subject to any disclaimer, the term of this patent is extended or adjusted under 35 U.S.C. 154(b) by 0 days.

This patent is subject to a terminal disclaimer.

(21) Appl. No.: 16/416,597

(22) Filed: May 20, 2019

(65) Prior Publication Data

US 2019/0304586 A1  Oct. 3, 2019

Related U.S. Application Data

(63) Continuation of application No. 15/032,741, filed as application No. PCT/TR2014/000386 on Oct. 20, 2014, now Pat. No. 10,296,724.

(30) Foreign Application Priority Data

Oct. 30, 2013 (TR) ................................ 2013/12557

(51) Int. Cl.
*G16H 20/30* (2018.01)
*G16H 20/40* (2018.01)

(52) U.S. Cl.
CPC ............ *G16H 20/30* (2018.01); *G16H 20/40* (2018.01)

(58) Field of Classification Search
None
See application file for complete search history.

(56) References Cited

U.S. PATENT DOCUMENTS

| 5,692,501 | A  | * | 12/1997 | Minturn | A61B 5/00 600/301 |
| 8,690,578 | B1 | * | 4/2014 | Nusbaum | G09B 19/00 434/127 |
| 9,665,873 | B2 | * | 5/2017 | Ackland | G16H 50/70 |
| 2003/0027688 | A1 | * | 2/2003 | Gordon | G16H 20/30 482/9 |
| 2005/0240434 | A1 | * | 10/2005 | Wooten | G16H 20/60 705/2 |

(Continued)

FOREIGN PATENT DOCUMENTS

WO  WO-2010041001 A1 * 4/2010 ............. G16H 20/30

*Primary Examiner* — Michael Tomaszewski
*Assistant Examiner* — Jay M. Patel
(74) *Attorney, Agent, or Firm* — Egbert, McDaniel & Swartz, PLLC

(57) ABSTRACT

A method in the field of health related fitness is disclosed for preparing and monitoring a customized exercise prescription based on scientific and concrete data and by activating all of the fitness components, and includes the process steps of dividing the strength component value into three separate sub components as lower extremity strength, upper extremity strength and trunk strength, creating an image of fitness map on the display (screen) which shows the ratios of fitness component values according to the age- and gender-related norms, determining exercise strategy by putting the fitness components of a person in order with respect to their priority of effect to health in accordance with the measurements of fitness components of a person, and preparing an exercise prescription which will provide simultaneous improvement of fitness components of a person.

20 Claims, 17 Drawing Sheets

(56) References Cited

U.S. PATENT DOCUMENTS

| | | | | |
|---|---|---|---|---|
| 2005/0240444 A1* | 10/2005 | Wooten | G16H 10/60 | |
| | | | | 705/3 |
| 2007/0197274 A1* | 8/2007 | Dugan | A63F 13/10 | |
| | | | | 463/7 |
| 2008/0046284 A1* | 2/2008 | Fisher | G16H 20/60 | |
| | | | | 705/2 |
| 2008/0161655 A1* | 7/2008 | Teller | A61B 5/7275 | |
| | | | | 600/300 |
| 2010/0022364 A1* | 1/2010 | Bocchicchio | A63B 21/068 | |
| | | | | 482/96 |
| 2011/0281249 A1* | 11/2011 | Gammell | G16H 20/30 | |
| | | | | 434/247 |
| 2012/0040799 A1* | 2/2012 | Jaquish | A63B 21/4035 | |
| | | | | 482/9 |
| 2012/0071733 A1* | 3/2012 | Grey | A61B 5/04012 | |
| | | | | 600/301 |
| 2012/0165703 A1* | 6/2012 | Bottum | G16H 50/30 | |
| | | | | 600/595 |
| 2013/0053990 A1* | 2/2013 | Ackland | A63B 24/0062 | |
| | | | | 700/91 |
| 2014/0089836 A1* | 3/2014 | Damani | G16H 20/10 | |
| | | | | 715/771 |

* cited by examiner

FIG. 10
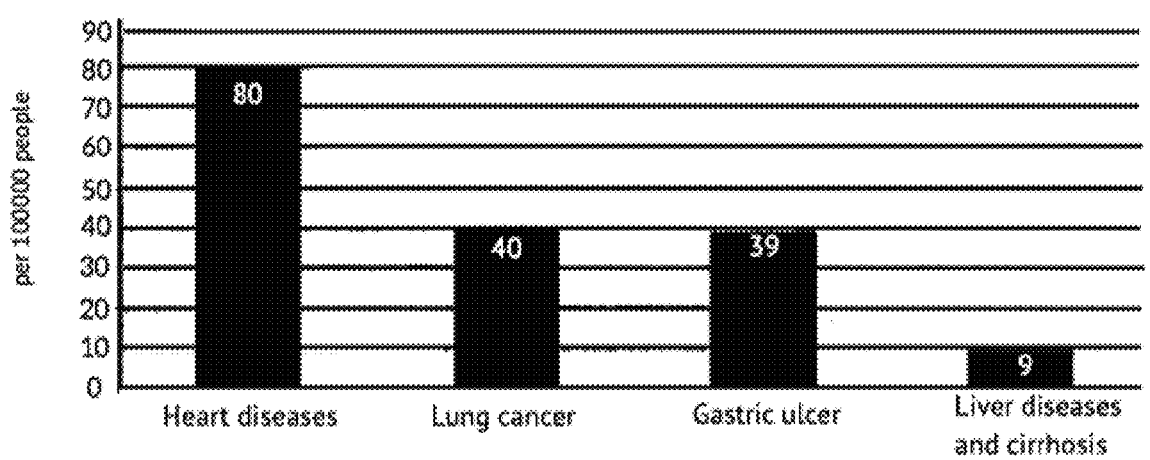
FIG. 11: Table 1

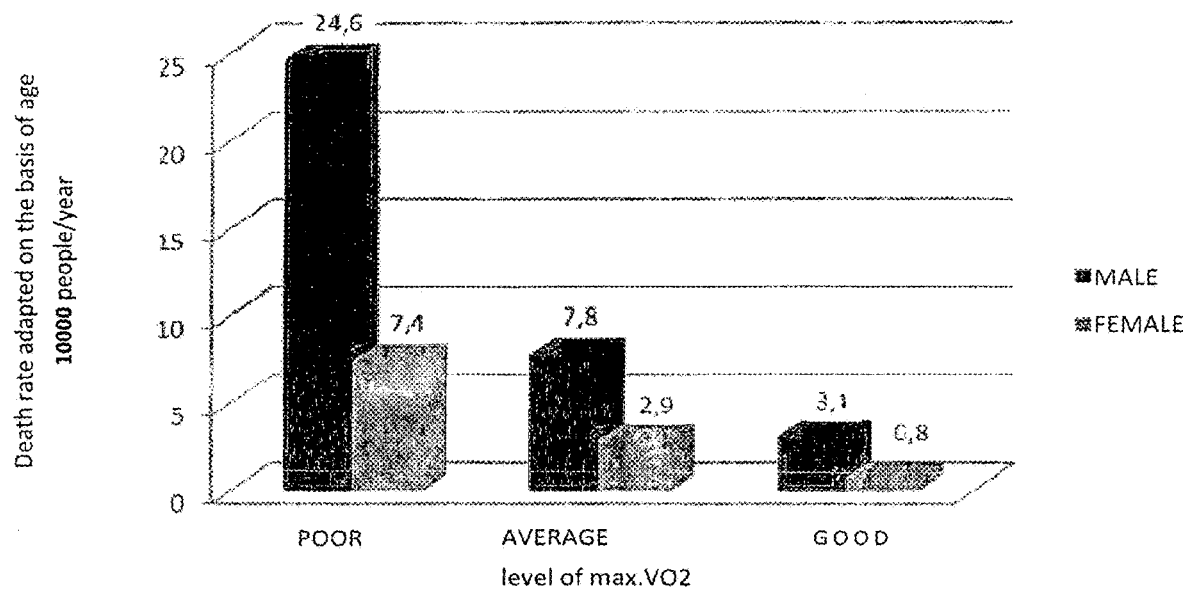
FIG. 12: Table 2
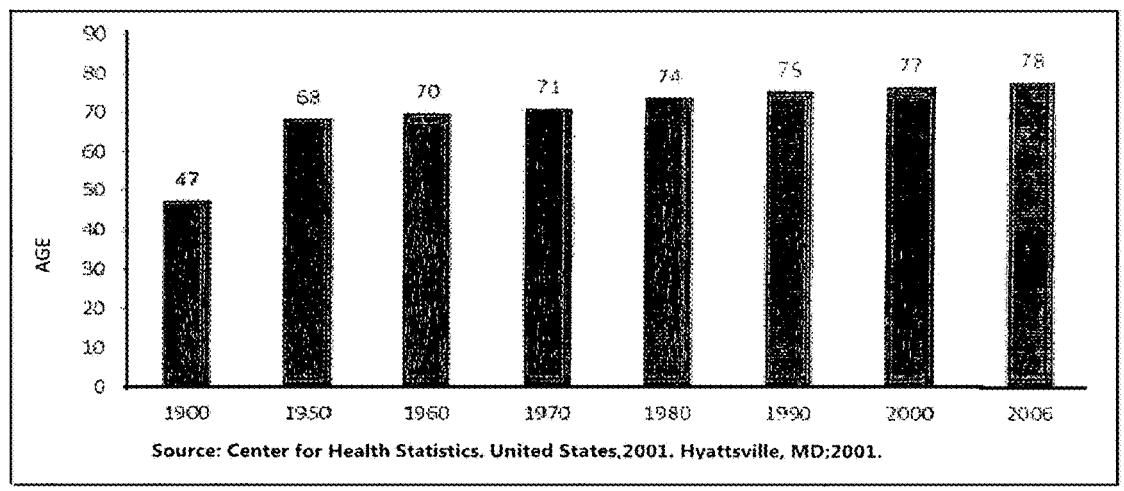
Table 3: Average lifespan of human being according to years
FIG. 13

Source: Department of Health and Human Services. Washinton DC:January 2000.
Table 4: Average lifespan of human being lived healthy and unhealthy Table 12: DIAGRAM OF RULES TO DETERMINE EXERCISE STRATEGY

| Frequency | Total Time | Strategy Code | Session Order | Primary Cardio (minutes) | Session Order | Cardio (minutes) | Session Order | Primary Strenght (minutes) | Session Order | Secondary Strenght (minutes) | Session Order | Primary Flexibility (minutes) | Session Order | Secondary Flexibility (minutes) | Total Time | Strategy Frequency |
|---|---|---|---|---|---|---|---|---|---|---|---|---|---|---|---|---|
| | | | | | | Tables of Cardio Strategy Frequencies and Times | | | | | | | | | | |
| 1 | 30 | 1.ST | 1 | 25 | | | | | | | | | 2 | 5 | 30 | 1 |
| 2 | 30 | 1.ST | 1 | 25 | | | | | | | | | 2 | 5 | 30 | 2 |
| 3 | 30 | 1.ST | 1 | 25 | | | | | | | | | 2 | 5 | 30 | 3 |
| 4 | 30 | 1.ST | 1 | 25 | | | | | | | | | 2 | 5 | 30 | 3 |
| 4 | 30 | 2.ST - a | | | | | 1 | 30 | | | | | | | 30 | 1 |
| 5 | 30 | 1.ST | 1 | 25 | | | | | | | | | 2 | 5 | 30 | 3 |
| 5 | 30 | 2.ST - a | | | | | 1 | 30 | | | | | | | 30 | 2 |
| 6 | 30 | 1.ST | 1 | 25 | | | | | | | | | 2 | 5 | 30 | 3 |
| 6 | 30 | 2.ST - a | | | | | 1 | 30 | | | | | | | 30 | 2 |
| 6 | 30 | 3.ST | | | | | | | | | 1 | 30 | | | 30 | 1 |
| 7 | 30 | 1.ST | 1 | 25 | | | | | | | | | 2 | 5 | 30 | 3 |
| 7 | 30 | 2.ST - a | | | | | 1 | 30 | | | | | | | 30 | 2 |
| 7 | 30 | 3.ST | | | | | | | | | 1 | 30 | | | 30 | 2 |
| 1 | 40 | 1.ST | 1 | 35 | | | | | | | | | 2 | 5 | 40 | 1 |
| 2 | 40 | 1.ST | 1 | 35 | | | | | | | | | 2 | 5 | 40 | 2 |
| 3 | 40 | 1.ST | 1 | 35 | | | | | | | | | 2 | 5 | 40 | 3 |
| 4 | 40 | 1.ST | 1 | 35 | | | | | | | | | 2 | 5 | 40 | 3 |
| 4 | 40 | 2.ST - a | | | | | 1 | 40 | | | | | | | 40 | 1 |
| 5 | 40 | 1.ST | 1 | 35 | | | | | | | | | 2 | 5 | 40 | 3 |
| 5 | 40 | 2.ST - a | | | | | 1 | 40 | | | | | | | 40 | 2 |
| 6 | 40 | 1.ST | 1 | 35 | | | | | | | | | 2 | 5 | 40 | 3 |
| 6 | 40 | 2.ST - a | | | | | 1 | 40 | | | | | | | 40 | 2 |
| 6 | 40 | 3.ST | | | | | | | | | 1 | 40 | | | 40 | 1 |
| 7 | 40 | 1.ST | 1 | 35 | | | | | | | | | 2 | 5 | 40 | 3 |
| 7 | 40 | 2.ST - a | | | | | 1 | 40 | | | | | | | 40 | 2 |
| 7 | 40 | 3.ST | | | | | | | | | 1 | 40 | | | 40 | 2 |
| 1 | 50 | 1.ST | 1 | 35 | | | | | 3 | 10 | | | 2 | 5 | 50 | 1 |
| 2 | 50 | 1.ST | 1 | 35 | | | | | 3 | 10 | | | 2 | 5 | 50 | 2 |
| 3 | 50 | 1.ST | 1 | 35 | | | | | 3 | 10 | | | 2 | 5 | 50 | 3 |
| 4 | 50 | 1.ST | 1 | 35 | | | | | 3 | 10 | | | 2 | 5 | 50 | 3 |
| 4 | 50 | 2.ST - a | | | | | 1 | 50 | | | | | | | 50 | 1 |
| 5 | 50 | 1.ST | 1 | 35 | | | | | 3 | 10 | | | 2 | 5 | 50 | 3 |
| 5 | 50 | 2.ST - a | | | | | 1 | 50 | | | | | | | 50 | 2 |
| 6 | 50 | 1.ST | 1 | 35 | | | | | 3 | 10 | | | 2 | 5 | 50 | 3 |
| 6 | 50 | 2.ST - a | | | | | 1 | 50 | | | | | | | 50 | 2 |
| 6 | 50 | 3.ST | | | | | | | | | 50 | 1 | | | 50 | 1 |
| 7 | 50 | 1.ST | 1 | 35 | | | | | 3 | 10 | | | 2 | 5 | 50 | 3 |
| 7 | 50 | 2.ST - a | | | | | 1 | 50 | | | | | | | 50 | 2 |
| 7 | 50 | 3.ST | | | | | | | | | 50 | 1 | | | 50 | 2 |

Table 13a: Rules for preparing exercise session depending on frequency and time in cardio strategy (1.ST.)

FIG. 16

| Tables of Cardio Strategy Frequencies and Times ||||||||||||||||
|---|---|---|---|---|---|---|---|---|---|---|---|---|---|---|---|
| Frequency | Total Time | Strategy Code | Session Order | Primary Cardio (minutes) | Session Order | Cardio (minutes) | Session Order | Primary Strenght (minutes) | Session Order | Secondary Strenght (minutes) | Session Order | Flexibility (minutes) | Session Order | Secondary Flexibility (minutes) | Total Time | Strategy Frequency |
| 1 | 60 | 1.ST | 1 | 35 | | | | | 3 | 20 | | | 2 | 5 | 60 | 1 |
| 2 | 60 | 1.ST | 1 | 35 | | | | | 3 | 20 | | | 2 | 5 | 60 | 2 |
| 3 | 60 | 1.ST | 1 | 35 | | | | | 3 | 20 | | | 2 | 5 | 60 | 3 |
| 4 | 60 | 1.ST | 1 | 35 | | | | | 3 | 20 | | | 2 | 5 | 60 | 3 |
| 4 | 60 | 2.ST - a | | | 2 | 20 | 1 | 35 | | | | | 3 | 5 | 60 | 1 |
| 5 | 60 | 1.ST | 1 | 35 | | | | | 3 | 20 | | | 2 | 5 | 60 | 3 |
| 5 | 60 | 2.ST - a | | | 2 | 20 | 1 | 35 | | | | | 3 | 5 | 60 | 2 |
| 6 | 60 | 1.ST | 1 | 35 | | | | | 3 | 20 | | | 2 | 5 | 60 | 3 |
| 6 | 60 | 2.ST - a | | | 2 | 20 | 1 | 35 | | | | | 3 | 5 | 60 | 2 |
| 6 | 60 | 3.ST | 1 | 20 | | | | | | | 2 | 40 | | | 60 | 1 |
| 7 | 60 | 1.ST | 1 | 35 | | | | | 3 | 20 | | | 2 | 5 | 60 | 3 |
| 7 | 60 | 2.ST - a | | | 2 | 20 | 1 | 35 | | | | | 3 | 5 | 60 | 2 |
| 7 | 60 | 3.ST | 1 | 20 | | | | | | | 2 | 40 | | | 60 | 2 |
| 1 | 70 | 1.ST | 1 | 35 | | | | | 3 | 25 | 3 | | 2 | 10 | 70 | 1 |
| 2 | 70 | 1.ST | 1 | 35 | | | | | 3 | 25 | 3 | | 2 | 10 | 70 | 2 |
| 3 | 70 | 1.ST | 1 | 35 | | | | | 3 | 25 | 3 | | 2 | 10 | 70 | 3 |
| 4 | 70 | 1.ST | 1 | 35 | | | | | 3 | 25 | | | 2 | 10 | 70 | 3 |
| 4 | 70 | 2.ST - a | | | 2 | 20 | 1 | 45 | | | | | 3 | 5 | 70 | 1 |
| 5 | 70 | 1.ST | 1 | 35 | | | | | 3 | 25 | | | 2 | 10 | 70 | 3 |
| 5 | 70 | 2.ST - a | | | 2 | 20 | 1 | 45 | | | | | 3 | 5 | 70 | 2 |
| 6 | 70 | 1.ST | 1 | 35 | | | | | 3 | 25 | | | 2 | 10 | 70 | 3 |
| 6 | 70 | 2.ST - a | | | 2 | 20 | 1 | 45 | | | | | 3 | 5 | 70 | 2 |
| 6 | 70 | 3.ST | 1 | 20 | | | | | | | 2 | 50 | | | 70 | 1 |
| 7 | 70 | 1.ST | 1 | 35 | | | | | 3 | 25 | | | 2 | 10 | 70 | 3 |
| 7 | 70 | 2.ST - a | | | 2 | 20 | 1 | 45 | | | | | 3 | 5 | 70 | 2 |
| 7 | 70 | 3.ST | 1 | 20 | | | | | | | 2 | 50 | | | 70 | 2 |
| 1 | 80 | 1.ST | 1 | 35 | | | | | 2 | 25 | 3 | 20 | | | 80 | 1 |
| 2 | 80 | 1.ST | 1 | 35 | | | | | 2 | 25 | 3 | 20 | | | 80 | 2 |
| 3 | 80 | 1.ST | 1 | 35 | | | | | 2 | 25 | 3 | 20 | | | 80 | 3 |
| 4 | 80 | 1.ST | 1 | 35 | | | | | 2 | 25 | 3 | 20 | | | 80 | 3 |
| 4 | 80 | 2.ST - a | | | 2 | 30 | 1 | 45 | | | | | 3 | 5 | 80 | 1 |
| 5 | 80 | 1.ST | 1 | 35 | | | | | 2 | 25 | 3 | 20 | | | 80 | 3 |
| 5 | 80 | 2.ST - a | | | 2 | 30 | 1 | 45 | | | | | 3 | 5 | 80 | 2 |
| 6 | 80 | 1.ST | 1 | 35 | | | | | 2 | 25 | 3 | 20 | | | 80 | 3 |
| 6 | 80 | 2.ST - a | | | 2 | 30 | 1 | 45 | | | | | 3 | 5 | 80 | 2 |
| 6 | 80 | 3.ST | 1 | 20 | | | | | | | 2 | 60 | | | 80 | 1 |
| 7 | 80 | 1.ST | 1 | 35 | | | | | 2 | 25 | 3 | 20 | | | 80 | 3 |
| 7 | 80 | 2.ST - a | | | 2 | 30 | 1 | 45 | | | | | 3 | 5 | 80 | 2 |
| 7 | 80 | 3.ST | 1 | 20 | | | | | | | 2 | 60 | | | 80 | 2 |
| 1 | 90 | 1.ST | 1 | 40 | | | | | 2 | 30 | 3 | 20 | | | 90 | 1 |
| 2 | 90 | 1.ST | 1 | 40 | | | | | 2 | 30 | 3 | 20 | | | 90 | 2 |
| 3 | 90 | 1.ST | 1 | 40 | | | | | 2 | 30 | 3 | 20 | | | 90 | 3 |
| 4 | 90 | 1.ST | 1 | 40 | | | | | 2 | 30 | 3 | 20 | | | 90 | 3 |
| 4 | 90 | 2.ST - a | | | 2 | 30 | 1 | 45 | | | | | 3 | 15 | 90 | 1 |
| 5 | 90 | 1.ST | 1 | 40 | | | | | 2 | 30 | 3 | 20 | | | 90 | 3 |
| 5 | 90 | 2.ST - a | | | 2 | 30 | 1 | 45 | | | | | 3 | 15 | 90 | 2 |
| 6 | 90 | 1.ST | 1 | 40 | | | | | 2 | 30 | 3 | 20 | | | 90 | 3 |
| 6 | 90 | 2.ST - a | | | 2 | 30 | 1 | 45 | | | | | 3 | 15 | 90 | 2 |
| 6 | 90 | 3.ST | 1 | 30 | | | | | | | 2 | 60 | | | 90 | 1 |
| 7 | 90 | 1.ST | 1 | 40 | | | | | 2 | 30 | 3 | 20 | | | 90 | 3 |
| 7 | 90 | 2.ST - a | | | 2 | 30 | 1 | 45 | | | | | 3 | 15 | 90 | 2 |
| 7 | 90 | 3.ST | 1 | 30 | | | | | | | 2 | 60 | | | 90 | 2 |

Table 13b: Rules for preparing exercise session depending on frequency and time in cardio strategy (1.ST.) - continued

FIG. 17

| Table of Strenght Strategy Frequencies and Times |||||||||||||||||||
|---|---|---|---|---|---|---|---|---|---|---|---|---|---|---|---|---|---|---|
| Frequency | Total Time | Strategy Code | Primary Strenght | Session Order | 1.ST Priority Area | Session Order | 2.st Priority Area | Session Order | 3.st Priority Area | Session Order | Primary Cardio | Session Order | Secondary Cardio | Session Order | Primary Flexibility | Session Order | Secondary Flexibility | Total Time | Strategy Frequency |
| | | | minutes | | Set to be Done | | Set to be Done | | Set to be Done | | | | | | | | | | |
| 1 | 30 | 2.ST - a | 30 | 1 | 4 | 2 | 4 | 3 | 4 | | | | | | | | | 30 | 1 |
| 2 | 30 | 2.ST - a | 30 | 1 | 4 | 2 | 4 | 3 | 4 | | | | | | | | | 30 | 2 |
| 3 | 30 | 2.ST - a | 30 | 1 | 4 | 2 | 4 | 3 | 4 | | | | | | | | | 30 | 2 |
| 3 | 30 | 1.ST | | | | | | | | 1 | 25 | | | | | 2 | 5 | 30 | 1 |
| 4 | 30 | 2.ST - a | 30 | 1 | 4 | 2 | 4 | 3 | 4 | | | | | | | | | 30 | 2 |
| 4 | 30 | 2.ST - b | 30 | 2 | 4 | 1 | 4 | 3 | 4 | | | | | | | | | 30 | 1 |
| 4 | 30 | 1.ST | 30 | | | | | | | 1 | 25 | | | | | 2 | 5 | 30 | 1 |
| 5 | 30 | 2.ST - a | 30 | 1 | 4 | 2 | 4 | 3 | 4 | | | | | | | | | 30 | 1 |
| 5 | 30 | 2.ST - b | 30 | 2 | 4 | 1 | 4 | 3 | 4 | | | | | | | | | 30 | 1 |
| 5 | 30 | 2.ST - c | 30 | 3 | 4 | 1 | 4 | 2 | 4 | | | | | | | | | 30 | 1 |
| 5 | 30 | 1.ST | | | | | | | | 1 | 25 | | | | | 2 | 5 | 30 | 2 |
| 6 | 30 | 2.ST - a | 30 | 1 | 4 | 2 | 4 | 3 | 4 | | | | | | | | | 30 | 2 |
| 6 | 30 | 2.ST - b | 30 | 2 | 4 | 1 | 4 | 3 | 4 | | | | | | | | | 30 | 1 |
| 6 | 30 | 2.ST - c | 30 | 3 | 4 | 1 | 4 | 2 | 4 | | | | | | | | | 30 | 1 |
| 6 | 30 | 1.ST | | | | | | | | 1 | 25 | | | | | 2 | 5 | 30 | 2 |
| 7 | 30 | 2.ST - a | 30 | 1 | 4 | 2 | 4 | 3 | 4 | | | | | | | | | 30 | 2 |
| 7 | 30 | 2.ST - b | 30 | 2 | 4 | 1 | 4 | 3 | 4 | | | | | | | | | 30 | 1 |
| 7 | 30 | 2.ST - c | 30 | 3 | 4 | 1 | 4 | 2 | 4 | | | | | | | | | 30 | 1 |
| 7 | 30 | 1.ST | | | | | | | | 1 | 25 | | | | | 2 | 5 | 30 | 2 |
| 7 | 30 | 3.ST | | | | | | | | | | | | 1 | 30 | | | 30 | 1 |
| 1 | 40 | 2.ST - a | 40 | 1 | 6 | 2 | 6 | 3 | 6 | | | | | | | | | 40 | 1 |
| 2 | 40 | 2.ST - a | 40 | 1 | 6 | 2 | 6 | 3 | 6 | | | | | | | | | 40 | 2 |
| 3 | 40 | 2.ST - a | 40 | 1 | 6 | 2 | 6 | 3 | 6 | | | | | | | | | 40 | 2 |
| 3 | 40 | 1.ST | | | | | | | | 1 | 35 | | | | | 2 | 5 | 40 | 1 |
| 4 | 40 | 2.ST - a | 40 | 1 | 6 | 2 | 6 | 3 | 6 | | | | | | | | | 40 | 2 |
| 4 | 40 | 2.ST - b | 40 | 2 | 6 | 1 | 6 | 3 | 6 | | | | | | | | | 40 | 1 |
| 4 | 40 | 1.ST | 40 | | | | | | | 1 | 35 | | | | | 2 | 5 | 40 | 1 |
| 5 | 40 | 2.ST - a | 40 | 1 | 6 | 2 | 6 | 3 | 6 | | | | | | | | | 40 | 1 |
| 5 | 40 | 2.ST - b | 40 | 2 | 6 | 1 | 6 | 3 | 6 | | | | | | | | | 40 | 1 |
| 5 | 40 | 2.ST - c | 40 | 3 | 6 | 1 | 6 | 2 | 6 | | | | | | | | | 40 | 1 |
| 5 | 40 | 1.ST | | | | | | | | 1 | 35 | | | | | 2 | 5 | 40 | 2 |
| 6 | 40 | 2.ST - a | 40 | 1 | 6 | 2 | 6 | 3 | 6 | | | | | | | | | 40 | 2 |
| 6 | 40 | 2.ST - b | 40 | 2 | 6 | 1 | 6 | 3 | 6 | | | | | | | | | 40 | 1 |
| 6 | 40 | 2.ST - c | 40 | 3 | 6 | 1 | 6 | 2 | 6 | | | | | | | | | 40 | 1 |
| 6 | 40 | 1.ST | | | | | | | | 1 | 35 | | | | | 2 | 5 | 40 | 2 |
| 7 | 40 | 2.ST - a | 40 | 1 | 6 | 2 | 6 | 3 | 6 | | | | | | | | | 40 | 2 |
| 7 | 40 | 2.ST - b | 40 | 2 | 6 | 1 | 6 | 3 | 6 | | | | | | | | | 40 | 1 |
| 7 | 40 | 2.ST - c | 40 | 3 | 6 | 1 | 6 | 2 | 6 | | | | | | | | | 40 | 1 |
| 7 | 40 | 1.ST | | | | | | | | 1 | 35 | | | | | 2 | 5 | 40 | 2 |
| 7 | 40 | 3.ST | | | | | | | | | | | | 1 | 40 | | | 40 | 1 |
| 1 | 50 | 2.ST - a | 50 | 1 | 7 | 2 | 7 | 3 | 7 | | | | | | | | | 50 | 1 |
| 2 | 50 | 2.ST - a | 50 | 1 | 7 | 2 | 7 | 3 | 7 | | | | | | | | | 50 | 2 |
| 3 | 50 | 2.ST - a | 50 | 1 | 7 | 2 | 7 | 3 | 7 | | | | | | | | | 50 | 2 |
| 3 | 50 | 1.ST | | | | | | | | 1 | 40 | | | | | 2 | 10 | 50 | 1 |
| 4 | 50 | 2.ST - a | 50 | 1 | 7 | 2 | 7 | 3 | 7 | | | | | | | | | 50 | 2 |
| 4 | 50 | 2.ST - b | 50 | 2 | 7 | 1 | 7 | 3 | 7 | | | | | | | | | 50 | 1 |
| 4 | 50 | 1.ST | 50 | | | | | | | 1 | 40 | | | | | 2 | 10 | 100 | 1 |
| 5 | 50 | 2.ST - a | 50 | 1 | 7 | 2 | 7 | 3 | 7 | | | | | | | | | 50 | 1 |
| 5 | 50 | 2.ST - b | 50 | 2 | 7 | 1 | 7 | 3 | 7 | | | | | | | | | 50 | 1 |
| 5 | 50 | 2.ST - c | 50 | 3 | 7 | 1 | 7 | 2 | 7 | | | | | | | | | 50 | 1 |
| 5 | 50 | 1.ST | | | | | | | | 1 | 40 | | | | | 2 | 10 | 50 | 2 |
| 6 | 50 | 2.ST - a | 50 | 1 | 7 | 2 | 7 | 3 | 7 | | | | | | | | | 50 | 2 |
| 6 | 50 | 2.ST - b | 50 | 2 | 7 | 1 | 7 | 3 | 7 | | | | | | | | | 50 | 1 |
| 6 | 50 | 2.ST - c | 50 | 3 | 7 | 1 | 7 | 2 | 7 | | | | | | | | | 50 | 1 |
| 6 | 50 | 1.ST | | | | | | | | 1 | 40 | | | | | 2 | 10 | 50 | 2 |
| 7 | 50 | 2.ST - a | 50 | 1 | 7 | 2 | 7 | 3 | 7 | | | | | | | | | 50 | 2 |
| 7 | 50 | 2.ST - b | 50 | 2 | 7 | 1 | 7 | 3 | 7 | | | | | | | | | 50 | 1 |
| 7 | 50 | 2.ST - c | 50 | 3 | 7 | 1 | 7 | 2 | 7 | | | | | | | | | 50 | 1 |
| 7 | 50 | 1.ST | | | | | | | | 1 | 40 | | | | | 2 | 10 | 50 | 2 |
| 7 | 50 | 3.ST | | | | | | | | | | | | 1 | 50 | | | 50 | 1 |

Table 14a: Rules for preparing exercise session depending on frequency and time in strenght strategy (2.ST.)

FIG. 18

Table of Strenght Strategy Frequencies and Times

| Frequency | Total Time | Strategy Code | Primary Strenght (minutes) | Session Order | 1.ST Priority Area (Set to be Done) | Session Order | 2.st Priority Area (Set to be Done) | Session Order | 3.st Priority Area (Set to be Done) | Session Order | Primary Cardio | Session Order | Secondary Cardio | Session Order | Primary Flexibility | Session Order | Secondary Flexibility | Total Time | Strategy Frequency |
|---|---|---|---|---|---|---|---|---|---|---|---|---|---|---|---|---|---|---|---|
| 1 | 60 | 2.ST - a | 35 | 1 | 5 | 2 | 5 | 3 | 5 | | | 4 | 20 | | | 5 | 5 | 60 | 1 |
| 2 | 60 | 2.ST - a | 35 | 1 | 5 | 2 | 5 | 3 | 5 | | | 4 | 20 | | | 5 | 5 | 60 | 2 |
| 3 | 60 | 2.ST - a | 35 | 1 | 5 | 2 | 5 | 3 | 5 | | | 4 | 20 | | | 5 | 5 | 60 | 3 |
| 4 | 60 | 2.ST - a | 35 | 1 | 5 | 2 | 5 | 3 | 5 | | | 4 | 20 | | | 5 | 5 | 60 | 2 |
| 4 | 60 | 2.ST - b | 35 | 2 | 5 | 1 | 5 | 3 | 5 | | | 4 | 20 | | | 5 | 5 | 60 | 2 |
| 5 | 60 | 2.ST - a | 35 | 1 | 5 | 2 | 5 | 3 | 5 | | | 4 | 20 | | | 5 | 5 | 60 | 2 |
| 5 | 60 | 2.ST - b | 35 | 2 | 5 | 1 | 5 | 3 | 5 | | | 4 | 20 | | | 5 | 5 | 60 | 2 |
| 5 | 60 | 2.ST - c | 35 | 3 | 5 | 1 | 5 | 2 | 5 | | | 4 | 20 | | | 5 | 5 | 60 | 1 |
| 6 | 60 | 2.ST - a | 35 | 1 | 5 | 2 | 5 | 3 | 5 | | | 4 | 20 | | | 5 | 5 | 60 | 2 |
| 6 | 60 | 2.ST - b | 35 | 2 | 5 | 1 | 5 | 3 | 5 | | | 4 | 20 | | | 5 | 5 | 60 | 2 |
| 6 | 60 | 2.ST - c | 35 | 3 | 5 | 1 | 5 | 2 | 5 | | | 4 | 20 | | | 5 | 5 | 60 | 2 |
| 7 | 60 | 2.ST - a | 35 | 1 | 5 | 2 | 5 | 3 | 5 | | | 4 | 20 | | | 5 | 5 | 60 | 2 |
| 7 | 60 | 2.ST - b | 35 | 2 | 5 | 1 | 5 | 3 | 5 | | | 4 | 20 | | | 5 | 5 | 60 | 2 |
| 7 | 60 | 2.ST - c | 35 | 3 | 5 | 1 | 5 | 2 | 5 | | | 4 | 20 | | | 5 | 5 | 60 | 2 |
| 7 | 60 | 3.ST | | | | | | | | | | | | 1 | 60 | | | 60 | 1 |
| 1 | 70 | 2.ST - a | 45 | 1 | 6 | 2 | 6 | 3 | 6 | | | 4 | 20 | | | 5 | 5 | 70 | 1 |
| 2 | 70 | 2.ST - a | 45 | 1 | 6 | 2 | 6 | 3 | 6 | | | 4 | 20 | | | 5 | 5 | 70 | 2 |
| 3 | 70 | 2.ST - a | 45 | 1 | 6 | 2 | 6 | 3 | 6 | | | 4 | 20 | | | 5 | 5 | 70 | 3 |
| 4 | 70 | 2.ST - a | 45 | 1 | 6 | 2 | 6 | 3 | 6 | | | 4 | 20 | | | 5 | 5 | 70 | 2 |
| 4 | 70 | 2.ST - b | 45 | 2 | 6 | 1 | 6 | 3 | 6 | | | 4 | 20 | | | 5 | 5 | 70 | 2 |
| 5 | 70 | 2.ST - a | 45 | 1 | 6 | 2 | 6 | 3 | 6 | | | 4 | 20 | | | 5 | 5 | 70 | 2 |
| 5 | 70 | 2.ST - b | 45 | 2 | 6 | 1 | 6 | 3 | 6 | | | 4 | 20 | | | 5 | 5 | 70 | 2 |
| 5 | 70 | 2.ST - c | 45 | 3 | 6 | 1 | 6 | 2 | 6 | | | 4 | 20 | | | 5 | 5 | 70 | 1 |
| 6 | 70 | 2.ST - a | 45 | 1 | 6 | 2 | 6 | 3 | 6 | | | 4 | 20 | | | 5 | 5 | 70 | 2 |
| 6 | 70 | 2.ST - b | 45 | 2 | 6 | 1 | 6 | 3 | 6 | | | 4 | 20 | | | 5 | 5 | 70 | 2 |
| 6 | 70 | 2.ST - c | 45 | 3 | 6 | 1 | 6 | 2 | 6 | | | 4 | 20 | | | 5 | 5 | 70 | 2 |
| 7 | 70 | 2.ST - a | 45 | 1 | 6 | 2 | 6 | 3 | 6 | | | 4 | 20 | | | 5 | 5 | 70 | 2 |
| 7 | 70 | 2.ST - b | 45 | 2 | 6 | 1 | 6 | 3 | 6 | | | 4 | 20 | | | 5 | 5 | 70 | 2 |
| 7 | 70 | 2.ST - c | 45 | 3 | 6 | 1 | 6 | 2 | 6 | | | 4 | 20 | | | 5 | 5 | 70 | 2 |
| 7 | 70 | 3.ST | 0 | | | | | | | 1 | 20 | | | 2 | 50 | | | 70 | 1 |
| 1 | 80 | 2.ST - a | 45 | 1 | 6 | 2 | 6 | 3 | 6 | | | 4 | 30 | | | 5 | 5 | 80 | 1 |
| 2 | 80 | 2.ST - a | 45 | 1 | 6 | 2 | 6 | 3 | 6 | | | 4 | 30 | | | 5 | 5 | 80 | 2 |
| 3 | 80 | 2.ST - a | 45 | 1 | 6 | 2 | 6 | 3 | 6 | | | 4 | 30 | | | 5 | 5 | 80 | 3 |
| 4 | 80 | 2.ST - a | 45 | 1 | 6 | 2 | 6 | 3 | 6 | | | 4 | 30 | | | 5 | 5 | 80 | 2 |
| 4 | 80 | 2.ST - b | 45 | 2 | 6 | 1 | 6 | 3 | 6 | | | 4 | 30 | | | 5 | 5 | 80 | 2 |
| 5 | 80 | 2.ST - a | 45 | 1 | 6 | 2 | 6 | 3 | 6 | | | 4 | 30 | | | 5 | 5 | 80 | 2 |
| 5 | 80 | 2.ST - b | 45 | 2 | 6 | 1 | 6 | 3 | 6 | | | 4 | 30 | | | 5 | 5 | 80 | 2 |
| 5 | 80 | 2.ST - c | 45 | 3 | 6 | 1 | 6 | 2 | 6 | | | 4 | 30 | | | 5 | 5 | 80 | 1 |
| 6 | 80 | 2.ST - a | 45 | 1 | 6 | 2 | 6 | 3 | 6 | | | 4 | 30 | | | 5 | 5 | 80 | 2 |
| 6 | 80 | 2.ST - b | 45 | 2 | 6 | 1 | 6 | 3 | 6 | | | 4 | 30 | | | 5 | 5 | 80 | 2 |
| 6 | 80 | 2.ST - c | 45 | 3 | 6 | 1 | 6 | 2 | 6 | | | 4 | 30 | | | 5 | 5 | 80 | 2 |
| 7 | 80 | 2.ST - a | 45 | 1 | 6 | 2 | 6 | 3 | 6 | | | 4 | 30 | | | 5 | 5 | 80 | 2 |
| 7 | 80 | 2.ST - b | 45 | 2 | 6 | 1 | 6 | 3 | 6 | | | 4 | 30 | | | 5 | 5 | 80 | 2 |
| 7 | 80 | 2.ST - c | 45 | 3 | 6 | 1 | 6 | 2 | 6 | | | 4 | 30 | | | 5 | 5 | 80 | 2 |
| 7 | 80 | 3.ST | | | | | | | | 1 | 20 | | | 2 | 60 | | | 80 | 1 |
| 1 | 90 | 2.ST - a | 45 | 1 | 6 | 2 | 6 | 3 | 6 | | | 4 | 30 | 5 | 15 | | | 90 | 1 |
| 2 | 90 | 2.ST - a | 45 | 1 | 6 | 2 | 6 | 3 | 6 | | | 4 | 30 | 5 | 15 | | | 90 | 2 |
| 3 | 90 | 2.ST - a | 45 | 1 | 6 | 2 | 6 | 3 | 6 | | | 4 | 30 | 5 | 15 | | | 90 | 3 |
| 4 | 90 | 2.ST - a | 45 | 1 | 6 | 2 | 6 | 3 | 6 | | | 4 | 30 | 5 | 15 | | | 90 | 2 |
| 4 | 90 | 2.ST - b | 45 | 2 | 6 | 1 | 6 | 3 | 6 | | | 4 | 30 | 5 | 15 | | | 90 | 2 |
| 5 | 90 | 2.ST - a | 45 | 1 | 6 | 2 | 6 | 3 | 6 | | | 4 | 30 | 5 | 15 | | | 90 | 2 |
| 5 | 90 | 2.ST - b | 45 | 2 | 6 | 1 | 6 | 3 | 6 | | | 4 | 30 | 5 | 15 | | | 90 | 2 |
| 5 | 90 | 2.ST - c | 45 | 3 | 6 | 1 | 6 | 2 | 6 | | | 4 | 30 | 5 | 15 | | | 90 | 1 |
| 6 | 90 | 2.ST - a | 45 | 1 | 6 | 2 | 6 | 3 | 6 | | | 4 | 30 | 5 | 15 | | | 90 | 2 |
| 6 | 90 | 2.ST - b | 45 | 2 | 6 | 1 | 6 | 3 | 6 | | | 4 | 30 | 5 | 15 | | | 90 | 2 |
| 6 | 90 | 2.ST - c | 45 | 3 | 6 | 1 | 6 | 2 | 6 | | | 4 | 30 | 5 | 15 | | | 90 | 2 |
| 7 | 90 | 2.ST - a | 45 | 1 | 6 | 2 | 6 | 3 | 6 | | | 4 | 30 | 5 | 15 | | | 90 | 2 |
| 7 | 90 | 2.ST - b | 45 | 2 | 6 | 1 | 6 | 3 | 6 | | | 4 | 30 | 5 | 15 | | | 90 | 2 |
| 7 | 90 | 2.ST - c | 45 | 3 | 6 | 1 | 6 | 2 | 6 | | | 4 | 30 | 5 | 15 | | | 90 | 2 |
| 7 | 90 | 3.ST | | | | | | | | 1 | 30 | | | 2 | 60 | | | 90 | 1 |

Table 14b: Rules for preparing exercise session depending on frequency and time in strenght strategy (2.ST) - continued

FIG. 19

| Frequency | Total Time | Strategy code | Session Order | Primary Cardio (minutes) | Session Order | Secondary Cardio (minutes) | Session Order | Primary Strenght (minutes) | Session Order | Secondary Strenght (minutes) | Session Order | Primary Flexibility (minutes) | Session Order | Secondary Flexibility (minutes) | Total Time | Strategy Frequencie |
|---|---|---|---|---|---|---|---|---|---|---|---|---|---|---|---|---|
| | | | | | | | | | | | | | | | | |
| 1 | 30 | 3.ST | | | | | | | | | 1 | 30 | | | 30 | 1 |
| 2 | 30 | 3.ST | | | | | | | | | 1 | 30 | | | 30 | 1 |
| 3 | 30 | 3.ST | | | | | | | | | 1 | 30 | | | 30 | 1 |
| 4 | 30 | 3.ST | | | | | | | | | 1 | 30 | | | 30 | 3 |
| 4 | 30 | 1.ST | 1 | 25 | | | | | | | | | 2 | 5 | 30 | 1 |
| 5 | 30 | 3.ST | | | | | | | | | 1 | 30 | | | 30 | 3 |
| 5 | 30 | 1.ST | 1 | 25 | | | | | | | | | 2 | 5 | 30 | 2 |
| 6 | 30 | 3.ST | | | | | | | | | 1 | 30 | | | 30 | 3 |
| 6 | 30 | 1.ST | 1 | 25 | | | | | | | | | 2 | 5 | 30 | 2 |
| 6 | 30 | 2.ST - a | | | | | 1 | 30 | | | | | | | 30 | 1 |
| 7 | 30 | 3.ST | | | | | | | | | 1 | 30 | | | 30 | 3 |
| 7 | 30 | 1.ST | 1 | 25 | | | | | | | | | 2 | 5 | 30 | 2 |
| 7 | 30 | 2.ST - a | | | | | 1 | 30 | | | | | | | 30 | 2 |
| 1 | 40 | 3.ST | | | | | | | | | 1 | 40 | | | 40 | 1 |
| 2 | 40 | 3.ST | | | | | | | | | 1 | 40 | | | 40 | 1 |
| 3 | 40 | 3.ST | | | | | | | | | 1 | 40 | | | 40 | 1 |
| 4 | 40 | 3.ST | | | | | | | | | 1 | 40 | | | 40 | 3 |
| 4 | 40 | 1.ST | 1 | 35 | | | | | | | | | 2 | 5 | 40 | 1 |
| 5 | 40 | 3.ST | | | | | | | | | 1 | 40 | | | 40 | 3 |
| 5 | 40 | 1.ST | 1 | 35 | | | | | | | | | 2 | 5 | 40 | 2 |
| 6 | 40 | 3.ST | | | | | | | | | 1 | 40 | | | 40 | 3 |
| 6 | 40 | 1.ST | 1 | 35 | | | | | | | | | 2 | 5 | 40 | 2 |
| 6 | 40 | 2.ST - a | | | | | 1 | 40 | | | | | | | 40 | 1 |
| 7 | 40 | 3.ST | | | | | | | | | 1 | 40 | | | 40 | 3 |
| 7 | 40 | 1.ST | 1 | 35 | | | | | | | | | 2 | 5 | 40 | 2 |
| 7 | 40 | 2.ST - a | | | | | 1 | 40 | | | | | | | 40 | 2 |
| 1 | 50 | 3.ST | | | | | | | | | 1 | 50 | | | 50 | 1 |
| 2 | 50 | 3.ST | | | | | | | | | 1 | 50 | | | 50 | 1 |
| 3 | 50 | 3.ST | | | | | | | | | 1 | 50 | | | 50 | 1 |
| 4 | 50 | 3.ST | | | | | | | | | 1 | 50 | | | 50 | 3 |
| 4 | 50 | 1.ST | 1 | 35 | | | | | 3 | 10 | | | 2 | 5 | 50 | 1 |
| 5 | 50 | 3.ST | | | | | | | | | 1 | 50 | | | 50 | 3 |
| 5 | 50 | 1.ST | 1 | 35 | | | | | 3 | 10 | | | 2 | 5 | 50 | 2 |
| 6 | 50 | 3.ST | | | | | | | | | 1 | 50 | | | 50 | 3 |
| 6 | 50 | 1.ST | 1 | 35 | | | | | 3 | 10 | | | 2 | 5 | 50 | 2 |
| 6 | 50 | 2.ST - a | | | | | 1 | 30 | | | 2 | 20 | | | 50 | 1 |
| 7 | 50 | 3.ST | | | | | | | | | 1 | 50 | | | 50 | 3 |
| 7 | 50 | 1.ST | 1 | 35 | | | | | 3 | 10 | | | 2 | 5 | 50 | 2 |
| 7 | 50 | 2.ST - a | | | | | 1 | 30 | | | 2 | 20 | | | 50 | 2 |

Table 15a: Rules for preparing exercise session değending on frequency and time in flexibility strategy (3.ST.)

FIG. 20

Table of Flexibility Strategy, Frequencies and Times

| Frequency | Total Time | Strategy code | Session Order | Primary Cardio (minutes) | Session Order | Secondary Cardio (minutes) | Session Order | Primary Strenght (minutes) | Session Order | Secondary Strenght (minutes) | Session Order | Primary Flexibility (minutes) | Session Order | Secondary Flexibility (minutes) | Total Time | Strategy Frequencie |
|---|---|---|---|---|---|---|---|---|---|---|---|---|---|---|---|---|
| 1 | 60 | 3.ST | | | | | | | | | 1 | 60 | | | 60 | 1 |
| 2 | 60 | 3.ST | | | | | | | | | 1 | 60 | | | 60 | 1 |
| 3 | 60 | 3.ST | | | | | | | | | 1 | 60 | | | 60 | 1 |
| 4 | 60 | 3.ST | | | | | | | | | 1 | 60 | | | 60 | 3 |
| 4 | 60 | 1.ST | 1 | 35 | | | | | 3 | 20 | | | 2 | 5 | 60 | 1 |
| 5 | 60 | 3.ST | | | | | | | | | 1 | 60 | | | 60 | 3 |
| 5 | 60 | 1.ST | 1 | 35 | | | | | 3 | 20 | | | 2 | 5 | 60 | 2 |
| 6 | 60 | 3.ST | | | | | | | | | 1 | 60 | | | 60 | 3 |
| 6 | 60 | 1.ST | 1 | 35 | | | | | 3 | 20 | | | 2 | 5 | 60 | 2 |
| 6 | 60 | 2.ST - a | | | | | 1 | 40 | | | 2 | 20 | | | 60 | 1 |
| 7 | 60 | 3.ST | | | | | | | | | 1 | 60 | | | 60 | 3 |
| 7 | 60 | 1.ST | 1 | 35 | | | | | 3 | 20 | | | 2 | 5 | 60 | 2 |
| 7 | 60 | 2.ST - a | | | | | 1 | 40 | | | 2 | 20 | | | 60 | 2 |
| 1 | 70 | 3.ST | | | | | 1 | 10 | | | 2 | 60 | | | 70 | 1 |
| 2 | 70 | 3.ST | | | | | 1 | 10 | | | 2 | 60 | | | 70 | 1 |
| 3 | 70 | 3.ST | | | | | 1 | 10 | | | 2 | 60 | | | 70 | 1 |
| 4 | 70 | 3.ST | | | | | 1 | 10 | | | 2 | 60 | | | 70 | 3 |
| 4 | 70 | 1.ST | 1 | 35 | | | | | 2 | 20 | 3 | 15 | | | 70 | 1 |
| 5 | 70 | 3.ST | | | | | 1 | 10 | | | 2 | 60 | | | 70 | 3 |
| 5 | 70 | 1.ST | 1 | 35 | | | | | 2 | 20 | 3 | 15 | | | 70 | 2 |
| 6 | 70 | 3.ST | | | | | 1 | 10 | | | 2 | 60 | | | 70 | 3 |
| 6 | 70 | 1.ST | 1 | 35 | | | | | 2 | 20 | 3 | 15 | | | 70 | 2 |
| 6 | 70 | 2.ST | | | | | 1 | 40 | | | 2 | 30 | | | 70 | 1 |
| 7 | 70 | 3.ST | | | | | 1 | 10 | | | 2 | 60 | | | 70 | 3 |
| 7 | 70 | 1.ST | 1 | 35 | | | | | 2 | 20 | 3 | 15 | | | 70 | 2 |
| 7 | 70 | 2.ST - a | | | | | 1 | 40 | | | 2 | 30 | | | 70 | 2 |
| 1 | 80 | 3.ST | | | | | 1 | 20 | | | 2 | 60 | | | 80 | 1 |
| 2 | 80 | 3.ST | | | | | 1 | 20 | | | 2 | 60 | | | 80 | 1 |
| 3 | 80 | 3.ST | | | | | 1 | 20 | | | 2 | 60 | | | 80 | 1 |
| 4 | 80 | 3.ST | | | | | 1 | 20 | | | 2 | 60 | | | 80 | 3 |
| 4 | 80 | 1.ST | 1 | 40 | | | | | 2 | 20 | 3 | 20 | | | 80 | 1 |
| 5 | 80 | 3.ST | | | | | 1 | 20 | | | 2 | 60 | | | 80 | 3 |
| 5 | 80 | 1.ST | 1 | 40 | | | | | 2 | 20 | 3 | 20 | | | 80 | 2 |
| 6 | 80 | 3.ST | | | | | 1 | 20 | | | 2 | 60 | | | 80 | 3 |
| 6 | 80 | 1.ST | 1 | 40 | | | | | 2 | 20 | 3 | 20 | | | 80 | 2 |
| 6 | 80 | 2.ST - a | | | | | 1 | 40 | | | 2 | 40 | | | 80 | 1 |
| 7 | 80 | 3.ST | | | | | 1 | 20 | | | 2 | 60 | | | 80 | 3 |
| 7 | 80 | 1.ST | 1 | 40 | | | | | 2 | 20 | 3 | 20 | | | 80 | 2 |
| 7 | 80 | 2.ST | | | | | 1 | 40 | | | 2 | 40 | | | 80 | 2 |
| 1 | 90 | 3.ST | | | | | 1 | 30 | | | 2 | 60 | | | 90 | 1 |
| 2 | 90 | 3.ST | | | | | 1 | 30 | | | 2 | 60 | | | 90 | 1 |
| 3 | 90 | 3.ST | | | | | 1 | 30 | | | 2 | 60 | | | 90 | 1 |
| 4 | 90 | 3.ST | | | | | 1 | 30 | | | 2 | 60 | | | 90 | 3 |
| 4 | 90 | 1.ST | 1 | 40 | | | | | 2 | 20 | 3 | 30 | | | 90 | 1 |
| 5 | 90 | 3.ST | | | | | 1 | 30 | | | 2 | 60 | | | 90 | 3 |
| 5 | 90 | 1.ST | 1 | 40 | | | | | 2 | 20 | 3 | 30 | | | 90 | 2 |
| 6 | 90 | 3.ST | | | | | 1 | 30 | | | 2 | 60 | | | 90 | 3 |
| 6 | 90 | 1.ST | 1 | 40 | | | | | 2 | 20 | 3 | 30 | | | 90 | 2 |
| 6 | 90 | 2.ST - a | | | | | 1 | 40 | | | 2 | 50 | | | 90 | 1 |
| 7 | 90 | 3.ST | | | | | 1 | 30 | | | 2 | 60 | | | 90 | 3 |
| 7 | 90 | 1.ST | 1 | 40 | | | | | 2 | 20 | 3 | 30 | | | 90 | 2 |
| 7 | 90 | 2.ST - a | | | | | 1 | 40 | | | 2 | 50 | | | 90 | 2 |

Table 15b: Rules for preparing exercise session değending on frequency and time in flexibility strategy (3.ST) - Continued

FIG. 21

| MaxVO2 NORMS (ml/min/kg) ||||||||
|---|---|---|---|---|---|---|---|
| CLASSIFICATION ||||||||
| | AGE | VERY WEAK | WEAK | MODERATE | AVERAGE | GOOD | VERY GOOD | PERFECT |
| Male | 20-24 | <32 | 32-37 | 38-43 | 44-50 | 51-56 | 57-62 | >62 |
| | 25-29 | <31 | 31-35 | 36-42 | 43-48 | 49-53 | 54-59 | >59 |
| | 30-34 | <29 | 29-34 | 35-40 | 41-45 | 46-51 | 52-56 | >56 |
| | 35-39 | <28 | 28-32 | 33-38 | 39-43 | 44-48 | 49-54 | >54 |
| | 40-44 | <26 | 26-31 | 32-35 | 36-41 | 42-46 | 47-51 | >51 |
| | 45-49 | <25 | 25-29 | 30-34 | 35-39 | 40-43 | 44-48 | >48 |
| | 50-54 | <24 | 24-27 | 28-32 | 33-36 | 37-41 | 42-46 | >46 |
| | 55-59 | <22 | 22-26 | 27-30 | 31-34 | 35-39 | 40-43 | >43 |
| | 60-65 | <21 | 21-24 | 25-28 | 29-32 | 33-36 | 37-40 | >40 |

Table 5: Data of MaxVO2 norms

Source: Shvartz E, Reibold RC:Aerobic fitness norms for males and females aged 6 to 75 years:a review.Aviat Space Environ Med; 61:3-11,1990.

FIG. 22

| All the Fitness components | Fitness component multiplier | Component score (male min.) | Component score (male max.) | Male min. | Male max. |
|---|---|---|---|---|---|
| maxv02 | 0.40 | 44.44 | 59.26 | 17.78 | 23.70 |
| lower extremity (e.g. leg press) | 0.15 | 17.95 | 32.05 | 2.69 | 4.81 |
| upper extremity (e.g. bench press) | 0.12 | 22.86 | 34.29 | 2.74 | 4.11 |
| body (pull-up with knees bent) | 0.08 | 40.00 | 60.00 | 3.20 | 4.80 |
| flexibility | 0.10 | 37.50 | 62.50 | 3.75 | 6.25 |
| body composition | 0.15 | 100.00 | 75.00 | 15.00 | 11.25 |
| FITNESS SCORE | | | | 45.16 | 54.93 |

Table 6: Sample of fitness score for a male at the age of 30 who has average levels of measurement in each fitness component

FIG. 23

| | | LOWER EXTREMITY FORCE NORMS (leg press) | | | | | |
|---|---|---|---|---|---|---|---|
| | AGE | VERY WEAK | WEAK | AVERAGE | GOOD | VERY GOOD | PERFECT |
| Male | ≤ 20 | ≤1.56 | 1.57 -1.79 | 1.80-1.92 | 1.93 - 2.09 | 2.10-2.82 | >2.82 |
| | 20-29 | ≤1.50 | 1.51-1.67 | 1.68-1.86 | 1.87 - 2.00 | 2.01 - 2.40 | >2.40 |
| | 30-39 | ≤1.42 | 1.43 -1.55 | 1.56-1.67 | 1.68 -1.80 | 1.81-2.20 | >2.20 |
| | 40-49 | ≤1.34 | 1.35 - 1.47 | 1.48 -1.58 | 1.59 -1.70 | 1.71 - 2.02 | >2.02 |
| | 50-59 | ≤1.21 | 1.22 -1.35 | 1.36 -1.49 | 1.50 -1.60 | 1.61 -1.90 | >1.90 |
| | 60 + | ≤1.15 | 1.16-1.26 | 1.27-1.39 | 1.40 -1.51 | 1.52 -1.80 | >1.80 |

Table 7
Source:Institute for Aerobics Research, Dallas, TX, 1994

FIG. 24

| UPPER EXTREMITY FORCE NORMS (bench press) ||||||||
| --- |--- |--- |--- |--- |--- |--- |--- |
| CLASSIFICATION ||||||||
| | AGE | VERY WEAK | WEAK | AVERAGE | GOOD | VERY GOOD | PERFECT |
| Male | ≤ 20 | ≤0.76 | 0.77 - 0.92 | 0.93 -1.09 | 1.10-1.22 | 1.23 -1.76 | >1.76 |
| | 20-29 | ≤0.72 | 0.73 - 0.89 | 0.90 -1.02 | 1.03 -1.17 | 1.18-1.63 | >1.63 |
| | 30-39 | ≤0.65 | 0.66 - 0.80 | 0.81-0.89 | 0.90 -1.00 | 1.01 -1.35 | >1.35 |
| | 40-49 | ≤0.59 | 0.60 - 073 | 0.74-0.81 | 0.82 - 0.89 | 0.90 -1.20 | >1.20 |
| | 50-59 | ≤0.53 | 0.54-0.65 | 0.66-0.72 | 0.73 - 0.80 | 0.81 -1.05 | >1.05 |
| | 60 + | ≤0.49 | 0.50 - 0.59 | 060 - 0.66 | 0.67-0.73 | 0.74 - 0.94 | >0.94 |

Table 8
Source: Institute for Aerobics Research. Dallas. TX. 1994

FIG. 25

| BODY FORCE NORMS (1' pull-up with knees bent) |||||||
| --- |--- |--- |--- |--- |--- |--- |
| CLASSIFICATION |||||||
| | AGE | BAD | MODERATE | AVERAGE | GOOD | VERY GOOD |
| MALE | 15-19 | ≤32 | 33-37 | 38-41 | 42-47 | ≥48 |
| | 20-29 | ≤28 | 29-32 | 33-36 | 37-42 | ≥43 |
| | 30-39 | ≤21 | 22-26 | 27-30 | 31-35 | ≥36 |
| | 40-49 | ≤16 | 17-21 | 22-25 | 26-30 | ≥31 |
| | 50-59 | ≤12 | 13-17 | 18-21 | 22-25 | ≥26 |
| | 60-69 | ≤6 | 07-11 | 12-16 | 17-22 | ≥23 |

Table 9
Source: The Canadian Physical activity. Fitness & Lifestyle Appraisal: CSEP's Plan for Healthy Active Living, 1996

FIG. 26

| | FLEXIBILITY (Sit & Reach) NORMS | | | | | |
|---|---|---|---|---|---|---|
| | | | CLASSIFICATION | | | |
| | AGE | BAD | MODERATE | AVERAGE | GOOD | VERY GOOD |
| Male | 15-19 | ≤23 | 24-28 | 29-33 | 34-38 | ≥39 |
| | 20-29 | ≤24 | 25-29 | 30-33 | 34-39 | ≥40 |
| | 30-39 | ≤22 | 23-27 | 28-32 | 33-37 | ≥38 |
| | 40-49 | ≤17 | 18-23 | 24-28 | 29-34 | ≥35 |
| | 50-59 | ≤15 | 16-23 | 24-27 | 28-34 | ≥35 |
| | 60-69 | ≤14 | 15-19 | 20-24 | 25-32 | ≥33 |

Table 10
Source: Institute for Aerobics Research, Dallas, TX, 1994

FIG. 27

| | BODY COMPOSITION (fat percentage) NORMS | | | | | |
|---|---|---|---|---|---|---|
| | | | CLASSIFICATION | | | |
| | AGE | VERY LOW | LOW | NORMAL | HIGH | VERY HIGH |
| Male | 20-29 | <7 | 7-9 | 10-19 | 20-25 | >25 |
| | 30-39 | <8 | 8-13 | 14-22 | 23-27 | >27 |
| | 40-49 | <9 | 9-16 | 17-24 | 25-29 | >29 |
| | 50-59 | <10 | 10-18 | 19-25 | 26-30 | >30 |
| | 60 + | <11 | 11-19 | 20-26 | 27-31 | >31 |

Table 11
Source: WHO (World Health Organisation)

FIG. 28

METHOD FOR PREPARING A CUSTOMIZED EXERCISE STRATEGY

CROSS-REFERENCE TO RELATED APPLICATIONS

The present application is a division of U.S. application Ser. No. 15/032,741, filed on Apr. 28, 2016, which issued as U.S. Pat. No. 10,296,724 on May 21, 2019.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

TECHNICAL FIELD

The present invention relates to method for preparing and monitoring a customized recipe of exercise by basing on scientific and solid data and by activating all of the fitness components, in the field of health related fitness.

In addition to the component which forms a basis for the traditionalized methods of preparing a customized exercise, which is used to help a person reach the norms desired in respect of cardiovascular health, muscular force and flexibility, the present invention relates to a method for preparing a customized strategy and recipe of fitness exercise which forms the orders of priority and scopes of components of fitness for health (component of cardiovascular resistance, component of muscular force, component of muscular flexibility and component of body composition) and which calculates and monitors the intensity and duration of performance depending on the time spent for exercise by factoring all of the components together after determining the current level of physical fitness according to the age and gender of a person.

BACKGROUND OF THE INVENTION

It is observed that today the time that one spends for him/herself and for maintaining his/her health is short and it is getting shorter. The diseases resulting from physical inactivity which begins affecting man's health have caused all the countries to run campaigns to encourage people to physical activities with the leadership of World Health Organization, have resulted in insufficiency of the budgets spent by the countries for health related expenses and have even become a serious threat for insurance and retirement systems.

FIT letters forming fitness word indicates the actual meaning of exercise. Principles of Frequency, Intensity, Time convert to exercise when applied to any physical activity and the physical activity must have a purpose. Today, since most people associate fitness with weight control in general, it has become a tradition to prepare a recipe of exercise only based on the values of body composition of a person (namely fat ratio, water ratio and fat-free mass of body). Recipe of exercise is prepared by ignoring measurable fitness components of risk factors (whether that person is sedentary or not, smokes or not, has a positive family history or not, has hyperlipidemia or not, has hypertension or diabetes or obesity) and actual health of a person (cardiovascular resistance, muscular force and muscular flexibility).

Basic fitness components are as follows:
Cardiovascular Resistance (maxVO2)
Muscular Force
Muscular Flexibility
Body Composition (fat ratio+fat-free mass)

While preparing a recipe of fitness exercise by traditional methods, importance and order and intensity of each fitness components, ratio of time spent for improving each component to total time of exercise are not calculated. In this calculation mostly body composition values are taken into consideration. Also, each body composition measurement device with different brands may vary in analyzing the data.

Traditional methods of fitness prescription are based on a body composition consisting of three types of data. Apart from that, exercises of cardiovascular capacity, muscular force and muscular flexibility are formed aimlessly and negligently without being based on any solid data and system. Health related exercise program is prepared by basing via the developed method a person's cardiovascular resistance, muscular force and muscular flexibility on the norms for relevant age and gender and by considering in the comparison of these norms depending on age and gender, by determining the priority and intensity of exercise after calculating the priority, scope and intensity of fitness components according to the comparison of the results of measured components.

As also stated above, while a recipe of exercise which is prepared by the traditional method is prepared only based on the data of body composition, a needed, healthy and right combination of exercise cannot be obtained since not all of the fitness components are taken into consideration.

As a consequence, due to the negative points explained above and the insufficiency of traditional methods for calculating exercise in this field, improvement or development is required to be made in the field of methods for preparing and monitoring strategy and recipe of exercise which will be different from the known methods.

OBJECTS OF THE INVENTION

The object of the invention is to solve the problems about the methods for preparing and monitoring strategy and recipe of exercise mentioned above and to improve the methods for preparing recipe of exercise by inspiring from the current situation.

An object of the invention is to avoid the wrong exercises within the current system and not to cause injury or death by way of cross checks by considering in all of the fitness components (cardiovascular resistance, muscular force, muscular flexibility) and the sub-units of these components which will affect the exercises to be prepared by an instructor and to be provided to candidates who want to do fitness.

Another object of the invention is to prepare a strategy of right and healthy exercise automatically according to a person's physical components by considering in the possibility that an instructor may not have all of the knowledge about cross-checking fitness components.

An object of the invention is to prepare a strategy and recipe of health related exercise for a person by basing the person's cardiovascular resistance, muscular force and muscular flexibility on the norms for relevant age and gender and by considering in the comparison of these norms depending on age and gender, by determining the priority and intensity of exercise after calculating the priority, scope and intensity of fitness components according to the comparison of the results of measured components.

Another object of the invention is to prepare a recipe of exercise which is the most advantageous for a person doing fitness.

Another object of the invention is to determine a detailed order of exercise.

Another main object of the invention is to determine personal fitness score.

Structural and characteristic properties of the invention and all of its advantages will be understood by way of the figures given below and the detailed description written with reference to these figures, and for this reason the assessment also need to be performed in consideration of these figures and this detailed description.

BRIEF DESCRIPTION OF THE SEVERAL VIEWS OF THE DRAWINGS

FIG. 10, view of time and frequency in the exercise session. (For example, it is an exercise session performed for 90 minutes a day, 3 days a week.)

FIG. 11 illustrates Table 1: Leading causes of death due to illness in Turkey.

FIG. 12 illustrates Table 2: Link between cardiovascular resistance and cardiovascular mortality.

FIG. 13 illustrates Table 3: Average lifespan of human being according to years.

FIG. 16 illustrates Table 13a) and FIG. 17 illustrates Table 13b): Rules for preparing exercise session depending on frequency and time in cardio strategy (1.ST).

FIG. 18 illustrates Table 14a) and FIG. 19 illustrates Table 14b): Rules for preparing exercise session depending on frequency and time in force strategy (2.ST).

FIG. 20 illustrates Table 15a) and FIG. 21 illustrates Table 15b): Rules for preparing exercise session depending on frequency and time in flexibility strategy (3.ST).

FIG. 22 illustrates Table 5: Data of MaxV02 norms.

FIG. 23 illustrates Table 6: a sample of fitness scores for a male at the age of 30 who has average levels of measurement in each fitness component.

FIG. 24 illustrates Table 7: Lower Extremity Force Norms (leg press).

FIG. 25 illustrates Table 8: Upper Extremity Force Norms (bench press).

FIG. 26 illustrates Table 9: Body Force Norms (1' pull-up with knees bent).

FIG. 27 illustrates Table 10: Flexibility (Sit & Reach) Norms.

FIG. 28 illustrates Table 11: Body Composition (fat percentage) Norms.

Figure 1:
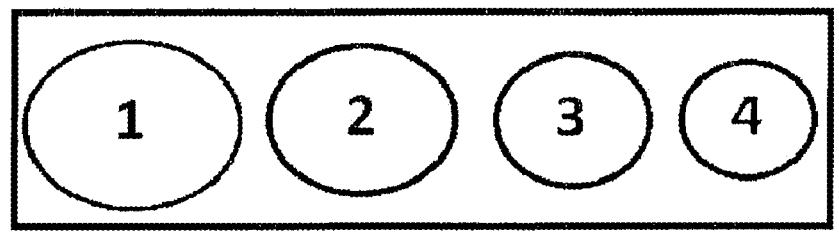
FIG. 1, view of health related fitness components in order of importance.
Figure 2:
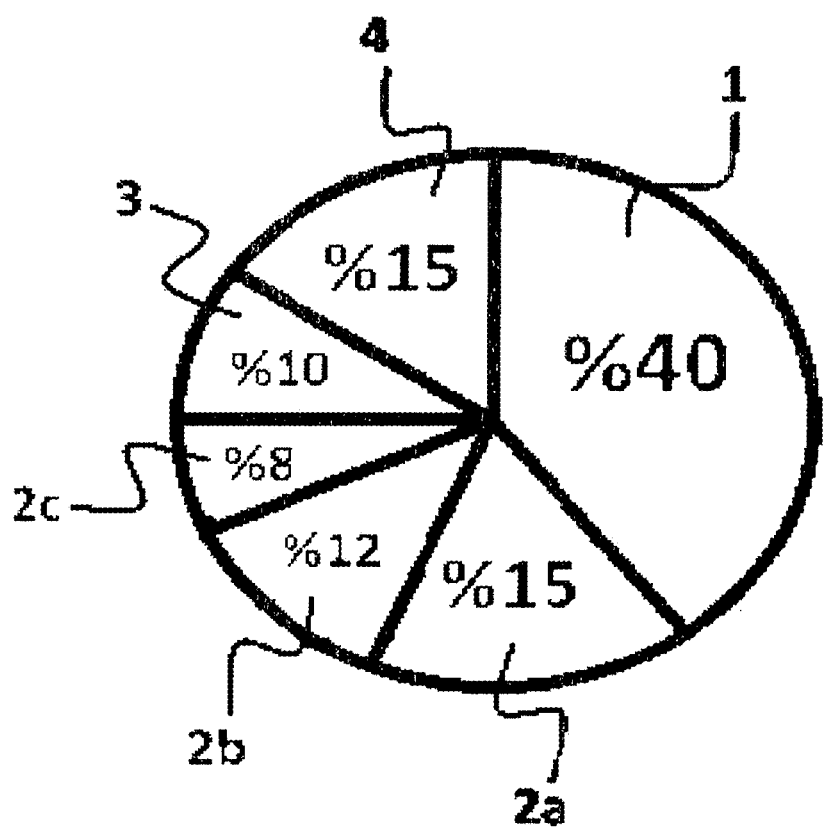
FIG. 2, view of fitness map on the display.

DESCRIPTION OF PART REFERENCES 1. axV02 (cardiovascular resistance component, cardiovascular capacity)
2. Muscular Force component (Force Component, Muscular Force)
   2a. Lower Extremity
   2b. Upper Extremity
   2c. Body
3. Muscular Flexibility Component
4. Body Composition Component
   Fat-Free Mass which is Another Component of Body Composition is Comprised of Protein, Mineral and Water.

Drawings do not have to be scaled and unnecessary details which are not required to understand the present invention might have been disregarded. Apart from that, elements which are at least considerably identical or which have at least considerably identical functions are indicated with the same number.

DETAILED DESCRIPTION OF THE INVENTION

In this detailed description, preferred steps of the method according to the invention are described only to help better understand the subject.

A method for preparing and monitoring a customized strategy and recipe of exercise by basing on scientific and solid data after determining the values of cardiovascular capacity (1), component of force (2), component of muscular flexibility (3), body composition (4) via measurement devices or other methods in the field of health related fitness characterized in that in order to improve each fitness component of a person, said method comprises the steps of considering in said values of cardiovascular capacity (1), component of force (2), component of muscular flexibility (3), component of body composition (4) in said method at a percentage in a total, calculating the ratio of values of a person's fitness components to the norms of fitness components for age and gender via said method;

calculating fitness component score separately for each component; calculating weighted total of fitness score based on the scores of all of the fitness components; preparing an image of fitness map and filling this map according to the said calculations in said method; monitoring the components in the map by determining their ratio to a whole and giving priority to them; allocating the biggest ratio to cardiovascular resistance(1)(maxV02), the second biggest ratio to component of muscular force, the third biggest ratio to body composition and the fourth biggest ratio to component of flexibility in said partition; determining an exercise strategy by putting these components in order in terms of priority of affecting health via said method in accordance with measurements of fitness components of a person; dividing said strategy of exercise into three as Cardio, Force and Flexibility strategies; determining an exercise session which will simultaneously improve the person's fitness components via said method within the frame of the above-said rules.

A person's body composition (4), cardiovascular resistance (1), muscular force (2) from different parts and flexibility level (3) are determined with the method according to the present invention. Depending on the frequency and time that a person will take for exercise per week, exercise strategy, exercise time and scope are designated according to objective norms (For example, Table 5, 7, 8, 9, 10 etc.) and solid rules (Table 12).

In said method for preparing a strategy and recipe of exercise: component of force (2) which is the second among the above-mentioned fitness components is divided into three separate sub-components (lower extremity force (2a), upper extremity force (2b) and body force (2c)). Five different components come up as a result of this division. After obtaining six fitness components by adding component of body composition (4) to these five different components, exercise strategies are determined systematically.

In said method for preparing strategy and recipe of exercise, the structuring of the prepared exercise strategy and thus recipe comprises three main topics in order to improve the relevant fitness components.

A) Creating fitness map: identifying component ratios and filling the map according to these ratios; determining fitness score B) Preparing exercise strategy C) Identifying the scope of exercise and program flow depending on exercise frequency and time after identifying the type of strategy First, distribution of fitness components in fitness map is determined on the basis of scientific researches. Afterwards, the degrees of fitness components in the space allocated for components in a whole body and their locations according to the norms are identified in accordance with the measurements of fitness components of a person. In accordance with the determinations for fitness components, three main components (cardiovascular resistance (1) exercises, muscular force (2) exercises, flexibility (3) exercises) are arranged in order of priority with respect to the importance of their effects to health. With the use of all of the data and factors, an exercise program is determined targeting simultaneous improvement of these components.

A) Creating Fitness Map: Identifying Component Ratios and Filling the Map According to these Ratios; Determining Fitness Score 1. Determination of Fitness Component Ratios in Fitness Map According to their importance for their effects in health, each fitness component is given a certain percentage (%) ratio, thus the substructure of map is created.

In determining the ratios, international data were considered in. Namely:

In the scientific platform, there are cardiovascular resistance (1), muscular force (2), muscular flexibility (3) and body composition (4) in the health related measurable fitness components. These components being closely related to physical health, their measurable nature, their norms depending on age and gender enables monitoring of a person for his/her physical suitability (fitness). For the concept of health, although there are mental and social health in addition to physical health the leading cause of death is coronary heart disease according to statistics (Table 1). The most important reason of this fact today is obesity and emergence of risk factors such as hyperlipidemia, diabetes, hypertension correspondingly.

When look at the fitness components, it is possible to state based on the scientific evidences that the most important component which affects the most important risk factor given above positively is the exercises which increase cardiovascular resistance (Table 2). Because of its contribution being the most important among others, cardiovascular resistance (maxV02-ml/dk/kg) (1) is given the ratio of 40% which is the biggest share in the fitness map.

According to the scientific evidences, the second most important fitness component related to physical health is muscular force (2) in today's conditions. The aim is to maintain the muscle mass which constitutes the force and to enable a person to continue his/her life without being in need of external support by increasing the muscular force. Average lifespan of a human being was 47 in 1900s and 78 in 2006 (Table 3). According to the statistical data, it is known that during the last 13 years of the 78 years of lifespan a person needs external support (Table 4). The most important reason of this situation is the age related sarcopenia which emerges as the lifespan of human being gets longer and the fact that person thus cannot perform the basic vital activities physically. Therefore, ACSM (American College of Sports Medicine) which is one of the most important institutions in the world in the field of exercise put resistance exercises in the exercise recipe officially in 1998. Based on all these data, lower extremity (2a) is allocated a share of 15%, upper extremity (2b) a share of 12%, body (2c) a share of 8% and force component (2) is therefore allocated a total share of 35%.

The third most important component which serves a function in preparing a strategy and recipe of exercise is the flexibility component (3). Today, it is known that flexibility of hind leg and back of a person take an important place since chronic low back pain is very common and it is a factor affecting quality of life. The smallest share at the rate of 10% is allocated to flexibility component (3) because of its role in survival of a person and in physiological actions although it is an important component.

Body composition (4); does not have any effect on the exercise strategy. However, especially since obesity affects health seriously, the share allocated to the body composition (4) is 15% in fitness map. The map mentioned in a preferred embodiment of the invention is a diagram.

2. Methods for Filling the Sections in Fitness Map

The relevant fitness component is measured and determined with direct or indirect methods and located in the map with the following method.

a) Cardiovascular Resistance (Max V02) (1)

With the method according to the invention, default minimum value of maxV02 (1) is accepted as zero (0) and default maximum value of maxV02 (1) as hundred (100) according to the norms for age and gender of the person. Its rate to the whole is calculated and its fill rate is determined in the space allocated to it in the map accurately. These processes are formulated by using the method of interpolation as follows:

(Measured value of fitness component−minimum value of fitness component)/(maximum value of fitness component−minimum value of fitness component)*100

Example: In Table 5, which is illustrated in FIG. 22, for a male between the age of 30-34, the value of 29 and lower corresponding to "very weak" state indicates 0 and the value of 56 and higher corresponding to perfect state indicates 100. If maxVO2 value of a male at the age of 30 is 41.0 ml/min/kg this falls into moderate class. For maxVO2 value of 41.0 ml/min/kg, component score on the scale of 100 is calculated as (41−29)/(56−29)*100=44.44.

Figures 3A, 3B:
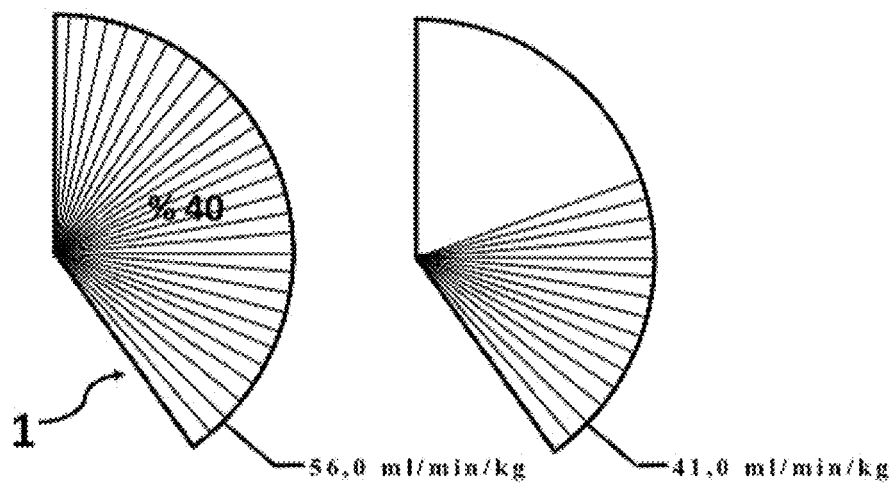
FIG. 3a, view of the state when the score of a fitness component fills the entire space reserved for it in the fitness map.
FIG. 3b, view of the state when the score of a fitness component cannot fill the entire space reserved for it in the map.

From this example on, maxVO2 (1) section of this person is given with a view in the map in FIG. 3b.

Filling of section of 40% allocated to cardiovascular resistance (1) depends on the increase in maxVO2 (1) value of a person. Accurate monitoring of a person's improvement is provided according to these map results.

The same route is followed also for other fitness components available in the map and hence monitoring of all of the fitness components is ensured.

After measures are put in each fitness component, one fitness score is calculated on the scale of 100 (Table 6, illustrated in FIG. 23) and a person's fitness score in respect of all of the fitness components is obtained by this way.

When a few different areas within a particular area are measured, their average is calculated. As force component (2) is divided into three different components (2a, 2b, 2c), there are many different tests to determine the level of each sub-component. Therefore, for instance, if two different tests are performed to determine upper extremity (2b) level, the results of both tests are taken and their average is displayed in the map.

After fill percentage of 6 different components (including sub-components of force component(2)) in respect of the spaces allocated for each is found on the same single map, fill percentage of the total of all values on the whole (namely 100%) map is determined. This result is the fitness score. The reason for obtaining fitness score is to see which fitness component is in which state and how fit a person is. The calculations of fitness score exemplified above, can be generalized as weighted sum of the scores of all the fitness components with the following mathematical expression:

$$\sum_{i=Fitness\,component} Component\,weight_i * Component\,score_i$$

Since the component scores are calculated by interpolation this formulation can be stated as follows:

$$\sum_{i=Fitness\,component} Component\,weight_i * \frac{(Measured\,value_i - Minimum\,value_i)}{(Maximum\,value_i - Minimum\,value_i)} * 100$$

b) Calculating Component Score for Body Composition

Unlike the other components, as the values of body composition (4) increase, human health is affected negatively. Therefore, body composition (4) component score of high fat rates is zero (0). Lower limit value of classification accepted normal (healthy) of the norms of the World Health Organization for age and gender is 100 as the body composition score. All of the values below this value, levels up to the essential fat rates for genders (3 percent for men, 12 percent for women) found in the scientific literature is 100. The decrease of a person's fat rate below the essential fat rate is also undesirable and expert advice is required in such situations. So, component score is seventy five (75) for the values below the essential fat rate. However, for other fat rates, component scores are calculated as follows:

$$Body\,composition\,component\,score = \begin{cases} 75 & Ratio < Essential\,value \\ 100 & Essential\,value \leq Ratio \leq MNNV \\ 75 + 25 * \frac{(MXNV - Ratio)}{(MXNV - MNNV)} & MNNV \leq Ratio \leq MXNV \\ 75 * \frac{(Maximum - Ratio)}{(Maximum - MXNV)} & MXNV \leq Ratio \leq Maximum \\ 0 & Maximum \leq Ratio \end{cases}$$

where
MNNV: Minimum normal value
MXNV: Maximum normal value

For instance, the minimum normal value (Min.Norm.Val.) to be used in the formulation above for a male at the age of 30 is 14 while the maximum normal value (Max.Norm.Val.) is 22 and the maximum value is 27. Ratio is the measured fat rate of a person. Therefore, for a person whose fat rate is 22 (22%), the component score is 75. Namely, as the weight of body composition (4) is 15 (15%), 75 percent (75%) of the body composition (4) component which has a section of 15 percent in the fitness map is filled. If fat rate of a person is 25 (25%), the component score is calculated as 75* (27−25)/(27−22)=30. In such situation 30 percent of the section of 15 percent becomes filled.

As to be explained in more detail under exercise strategy topic, the share that the measure for each fitness component gets in the map, actually determines the customized exercise strategy as well. Thus, the share of a component in the map also decides whether that component has priority in the exercise strategy. In the traditional methods for determining exercise, criterion of priority is not evaluated for fitness components and the order is not made according to the objective criteria and solid data. Cardiovascular exercises, resistance and flexibility exercises are applied negligently.

When all of the fitness components calculated with the above-mentioned methods are put in the sections allocated to them after being compared in accordance with the norms, it enables obtaining solid data in respect of which component a person needs to improve to what extent.

Figure 4:
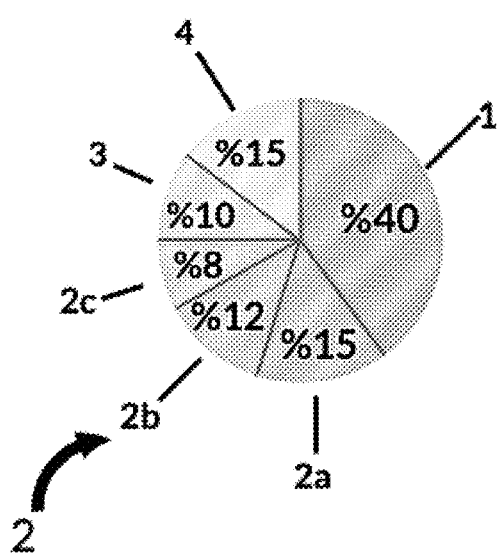
FIG. 4, view of the ideal state of fitness components of a person.
Figure 5:
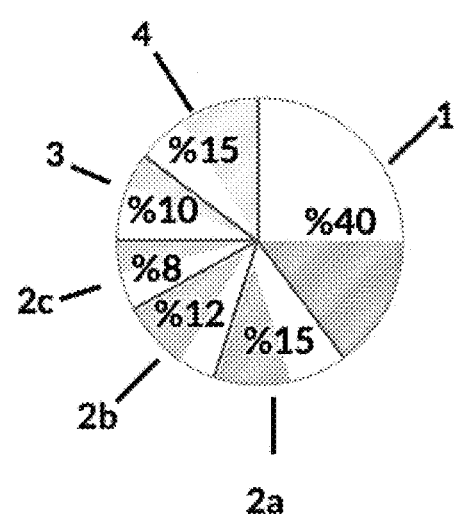
FIG. 5, view of the state of fitness components of a person which need to be improved.
Figure 6:
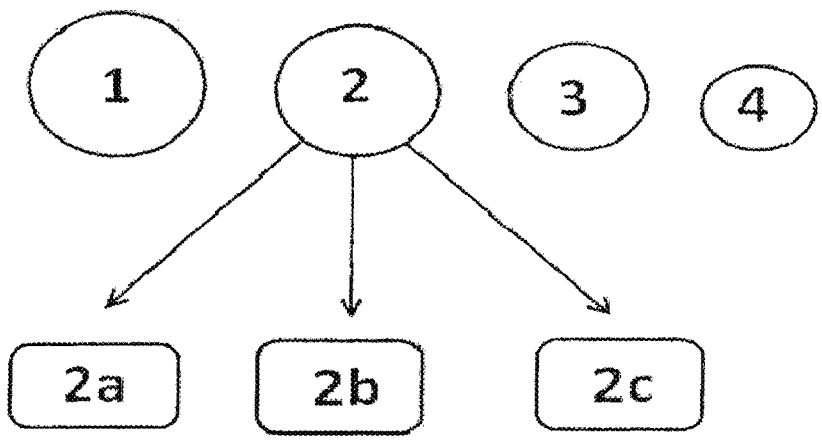
FIG. 6, general view of fitness components and sub-components of force component.

While the state of a person's physical suitability is concretely understood as the sections of health related fitness components are filled, component sections of a person who is not in good shape have gaps (FIG. 4). Another aim of the sections divided according to the priority of different components is to create and monitor simultaneous program for the targets determined in accordance with the map result. Also measures are kept in the system database at certain time intervals.

As the personal data evaluated according to the norms at regular intervals improve, fill ratio of the relevant section in the map increases. Exercise strategy and exercise recipe to be applied varies accordingly. According to the ratio of data to each other obtained with the method for activating six different components which provide monitoring of personal fitness map which forms the map and which is the subject of the invention, exercise strategy and thus exercise recipe is determined.

In the developed method, three different main fitness components (cardiovascular resistance (1), muscular force (2), muscular flexibility (3)) and also muscular force (2) are evaluated in also three different sub-components (lower extremity (2a) force, upper extremity (2b) force and body (2c) force) for preparing exercise strategy and the exercise recipe, and with the addition of body composition to all of these components, the exercise strategy according to the present invention is created according to six different components in total. Body composition remains passive in the method of creating exercise. In FIG. 4, distribution of components in their six-chamber sections are shown.

B) Preparing Exercise Strategy

In consideration of the data for health related fitness components in the fitness map (except for body composition (4)), order of priority is determined as explained above.
1. Cardiovascular Resistance (maxV02) (1)
2. Muscular Force (2)
    a—lower extremity (2a)
    b—upper extremity (2b)
    c—body (2c)
3. Muscular Flexibility (3)

The way how the rules for creating exercise strategy work is determined as follows:

In order to provide a healthy and proportional physical development of a person, first there is an aim of achieving the fill capacity of 50% allocated for each component in the map by referring to the norms.

Rules Determining Exercise Strategy (Table 12):
1. maxV02 (1) value of a person needs to be lower than the half of the space allocated to maxV02 (1) (<50%) in the map in order to select a cardio strategy. Once these conditions are met, exercise recipe is prepared according to this strategy.
2. If the average of force components (2) of a person is lower than the half of the space allocated to it (<50%) in the map and at the same time maxV02 (1) value of the person needs to be higher than the half of the space allocated to maxV02 (1) (>50%) in order to select a force strategy. Once these conditions are met, exercise recipe is prepared according to force strategy.
    a. In the exercise strategy where force component (2) has priority, force components (2) are evaluated separately and order is calculated accordingly. However, lower extremity (2a) from force components (2) is not put consecutively in cardiovascular exercises.
3. If the value of flexibility components (3) of a person is lower than the half of the space allocated to flexibility (<50%) and at the same time maxV02 (1) value and force (2) value of the person need to be higher than the half of the space allocated to them (>50%) in order to select a flexibility strategy. Once the relevant conditions are met, exercise recipe is prepared according to flexibility strategy.
4. If body composition (4) exceeds the limit in terms of fat rate, medical support (dietary program etc.) is recommended. Body composition (4) component does not have any effect in the determination of exercise strategy.
5. After components first reach 50% of the spaces allocated to them, the same route is followed to enable reaching 75% and then 100% in consideration of the conditions in the same way.

Figure 7:
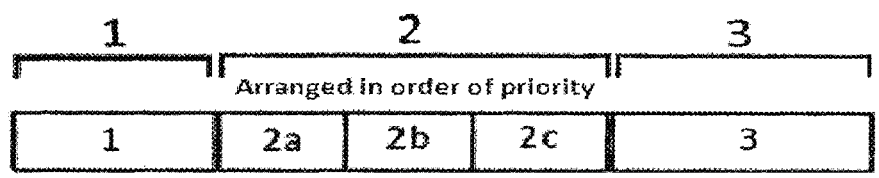
FIG. 7, graphical view of priority in the cardio strategy which comes first among the 3 types of exercise strategy.
Figure 8:
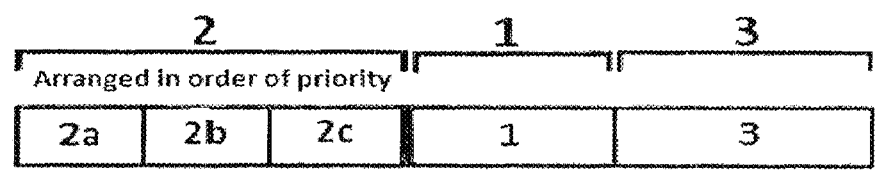
FIG. 8, graphical view of priority in the force strategy which comes second among the 3 types of exercise strategy.
Figure 9:
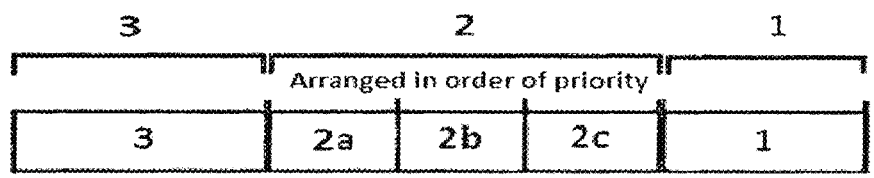
FIG. 9, graphical view of priority in the flexibility strategy which comes third among the 3 types of exercise strategy.
Figure 14:
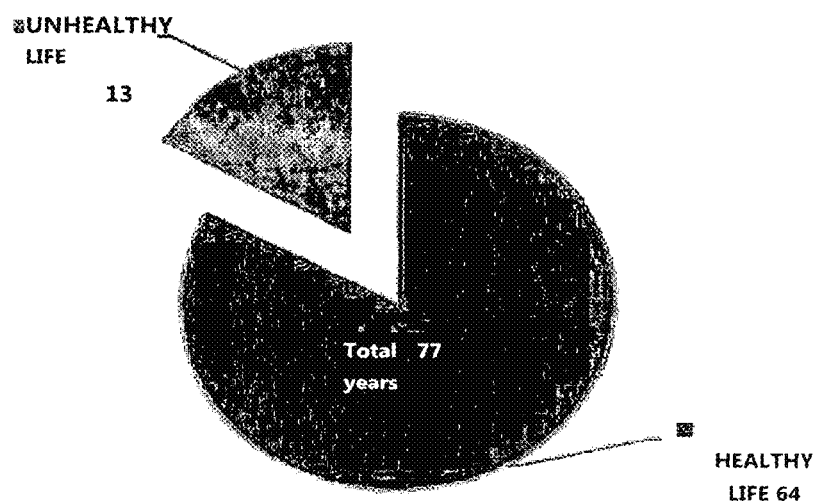
FIG. 14 illustrates Table 4: Average lifespan of human being lived healthy and unhealthy.
Figure 15:
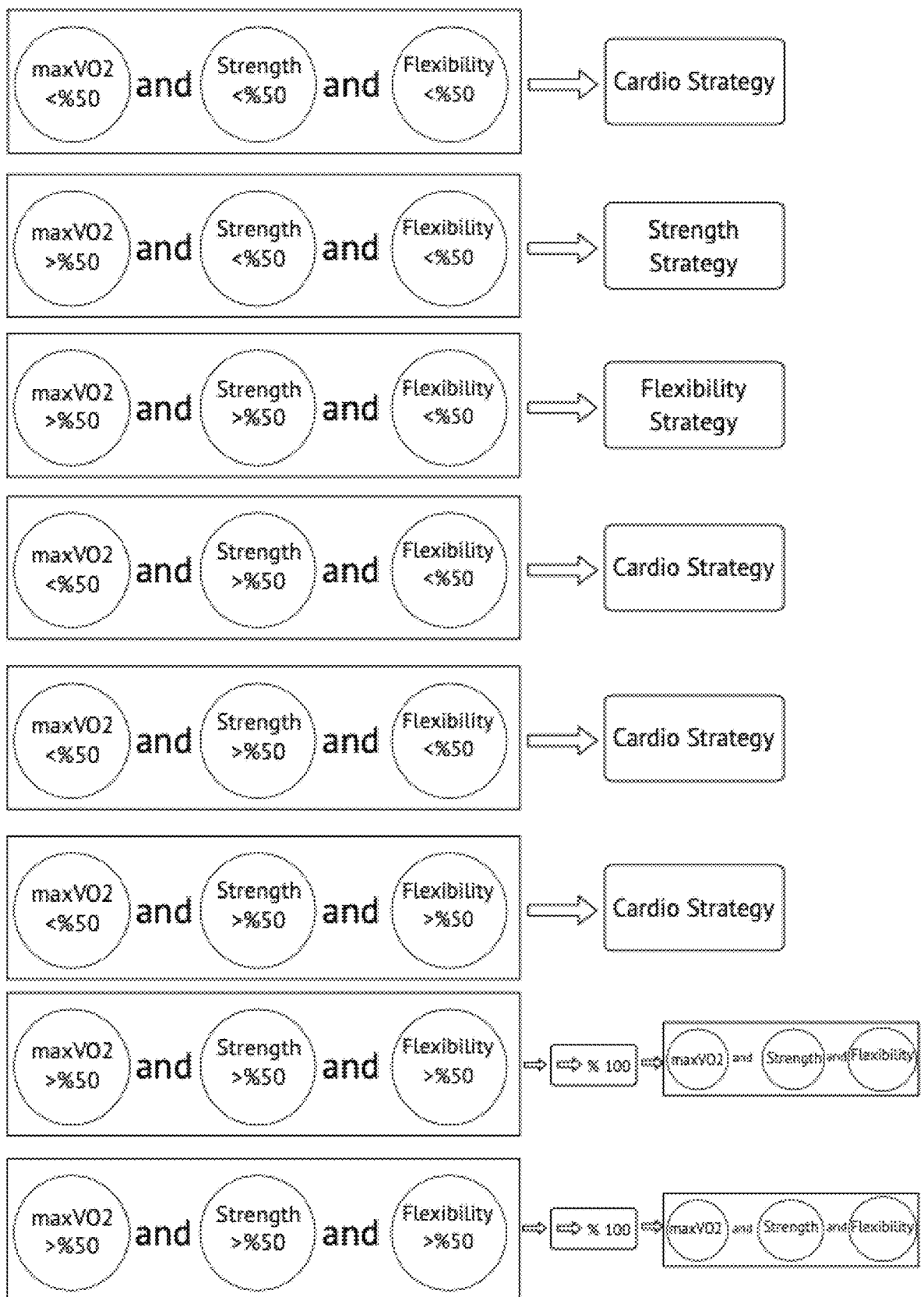
FIG. 15 illustrates Table 12: Diagram of rules to determine exercise strategy.

According to these conditions, a total of three different exercise strategies are prepared on customized basis (FIG. 7, FIG. 8, FIG. 9).

C) Identifying the Scope of Exercise and Program Flow for Each Exercise Session Depending on Exercise Frequency and Time after Identifying the Type of Strategy After the type of strategy is determined, determination of an exercise program for each exercise session, according to the frequency and time spared for exercise, for the improvement of fitness components and in accordance with the aims, and the rules therefor:

At the same time, in the exercise strategy: with the purpose of determining the order of exercise, in order to put forth the differences of components in terms of aim and intensity, each component is divided into two and a new terminology is created as follows:
    Cardio component as "PRIMARY CARDIO" and "SECONDARY CARDIO";
    Force component as "PRIMARY FORCE" and "SECONDARY FORCE";
    Flexibility component as "PRIMARY FLEXIBILITY" and "SECONDARY FLEXIBILITY".

As force component consists of three different sub-components (lower extremity, upper extremity and body), average value of three components are considered in. These values are not considered in the traditional method for calculating fitness exercise.

Depending on the frequency (1, 2, 3, 4, 5, 6, 7) and time (30', 40', 50', 60', 70', 80', 90') which can be spared for exercise, it is determined how much time and which frequency will be spared for which fitness component in each exercise session (FIG. 10).

Before describing the general rules applied for this determination and the operating principles of components, some of the terms found in the description of the method for preparing strategy and recipe of fitness exercise according to the present invention are given below:
1. PRIMARY CARDIO
2. SECONDARY CARDIO
3. PRIMARY FORCE
4. SECONDARY FORCE
5. PRIMARY FLEXIBILITY
6. SECONDARY FLEXIBILITY The importance of priority rule in respect of fitness components is great. There are three different sources of energy in human body physiologically. The one with the lowest rate of presence in our bodies is the source of carbohydrate. For example, in the body of a person with a weight of 70 kg and a fat rate of 14%, there is a source of energy with 88200 kcal from fat and approximately 2000 kcal from carbohydrate. Therefore, when it is considered that time of exercise also depends on these sources of energy, it is not possible to improve all of the fitness components simultaneously and equally in an exercise session in terms of energy system.

The fact that it is impossible for all of the components to operate in full performance in the same session in terms of both time and energy, makes the development of objective strategies based on the data available in respect of the priority and order of fitness components (negative effects caused to the performance of each other) necessary.

The frequency and scope that ACSM, which is one of the most important institutions in the world in the field of exercise, recommends are as follows:
    With respect to cardiovascular resistance (1); 3-7/days a week; 20-60 minutes,
    With respect to muscular force (2); 2-3/days a week; at least 1 set (8-12 runs) of 8-10 exercises,
    With respect to flexibility (3); exercises of at least 15 minutes with 15-30 second breaks during 4 sets.

Keeping in mind that that the primary aim of the exercise is to reach health, it is obvious that it is important to manage time spared for exercise in order to contribute to health by way of exercise. From this point on, the developed method for creating strategy and recipe of exercise is actually based on the logic of granting priority in terms of both fitness components and sub-components of force components (2) and administered with certain rules. Thus, the need for applying each fitness component in PRIMARY and SECONDARY degrees comes up. According to the strategy determined by using these terms, the duty of enabling reaching the primary aim lies on "PRIMARY" type while "SECONDARY" type is applied for maintaining purposes when there is increase in the opportunities of time and frequency.

Descriptions of Terms

1. Primary Cardio:
a) In terms of intensity of exercise, (provided that there is no limitation with regard to the risk factors of the person) upper limit may extend to 85% of maxV02 (1).
b) It is applied to the situation where cardiovascular resistance has priority.
c) Its primary aim is to improve the cardiovascular capacity (1) of the person.
2. Secondary Cardio:
a) In terms of intensity of exercise, upper limit may extend to 60% of maxV02 (1).
b) It is applied to the strategies where cardiovascular resistance does not have priority.
c) It always precedes the secondary flexibility.
d) Its primary aim is to provide energy consumption in aerobic environment.
3. Primary Force:
a) In terms of intensity of exercise, 6 runs are utilized corresponding to the upper limit of 85%.
b) It is applied to the situations where muscular force (2) has priority.
c) Its primary aim is to improve force.
4. Secondary Force:
a) In terms of intensity of exercise, 10 runs are utilized corresponding to the upper limit of 75%.
b) It is applied to the situations where muscular force (2) does not have priority.
c) Its primary aim is to maintain force.
5. Primary Flexibility:
a) In terms of scope of exercise, it is used to improve flexibility of joints of human body.
b) It is applied to the situations where flexibility has priority.
c) Meaning of its scope is minimum 30 minutes per session.
6. Secondary Flexibility:
a) In terms of scope of exercise, it is applied to let the muscles get into their former shape (pre-exercise shape) at the end of exercises which affect muscular flexibility (3) negatively (e.g.: especially cardiovascular exercises where movement area of muscles of legs is limited).
b) It is applied definitely after cardio exercises.
c) Meaning of scope is minimum 5 and maximum 10 minutes.

General Rules Applied for Exercise Sessions and Operating Principles of Components:
a) In a Session where Primary Cardio is Performed, Primary Force Exercises Cannot be Performed.
Cardiovascular exercises are the exercises performed to improve cardiovascular, circulatory and respiratory systems. Therefore, the primary aim of the method for preparing health-related strategy and recipe of exercise is to eliminate the risk factors which cause coronary heart diseases. The reason of why these kinds of exercises strengthen cardiovascular and circulatory systems is the operation of muscles of legs used during these exercises. It is important to emphasize that heart gains strength by being exposed to pressurized blood from legs and our functional capacity depends on this action. These exercises are the exercises where energy consumption reaches the highest levels among the health related fitness components. Accordingly, due to the decrease in the source of energy in the body and especially the prostration of muscles of legs, the new method does not comprise force (2) exercises (PRIMARY FORCE) of high intensity following cardiovascular (1) exercises (PRIMARY CARDIO). However, there are resistance exercises of medium intensity (SECONDARY FORCE) in order to maintain the muscular force and to provide "stimulus" to muscles.

b) In the Sessions where Primary and Secondary Cardio are Performed, Flexibility Exercises are Performed, Secondary Flexibility is Applied if the Time Spared for Flexibility Exercise is Up to 10 Minutes or Primary Flexibility is Applied if it is Longer than 10 Minutes.
In the course of cardiovascular exercises, flexibility of muscles and joints are affected negatively in the long term unless flexibility exercises are performed after cardiovascular exercises because especially the joints of hips and knees use a short angle of their range of motion. Flexibility exercises need to be performed in order to prevent these joints from losing their flexibility and to enable muscles of legs to get into their pre-exercise shape. Flexibility exercise (SECONDARY FLEXIBILITY) to be performed for less than 10 minutes depending on the time spared for flexibility (3) is for bringing the muscles into their former (pre-exercise) shape. In accordance with the strategy and the time of session, flexibility (PRIMARY FLEXIBILITY) exercises are performed in order to improve the flexibility of joints for more than 10 minutes.
Since cardiovascular (SECONDARY CARDIO) exercises not suitable for improvement are to be performed after force exercises, SECONDARY FLEXIBILITY is performed in order to bring the muscles into their former shape after the exercise.

c) In the Session where Primary Force is Performed, Primary Cardio Exercises are not Performed.
This rule used in the method according to the invention is a rule created in the same logic as explained in the "a" paragraph, 7th line, (page 16). Improving muscular force (2) is one of the most important investments made to maintain health and life quality of human being. The increase in force depends on the principle of over loading performed with resistance exercises. In short, it is a process performed by leaving muscle under a load which it cannot bear and to cause muscle to renew itself with an increasing protein synthesis. When consider the basic muscle groups (legs, hips, back, chest, shoulders, forearms, triceps, abdomen, waist etc.); it is possible to state that an exercise performed to increase force requires a significant time. The time spared in such exercises, due to the energy consumed and exercises of high intensity in relation with muscles of legs, PRIMARY CARDIO exercise primary aim of which is to improve cardiovascular capacity is not included following PRIMARY FORCE primary aim of which is to improve force. However, according to the strategy and time of session, in the sessions where PRIMARY FORCE is performed, SECONDARY CARDIO exercises performed in low or medium intensity may be included in order to provide energy consumption.

As force (2) exercises, especially open kinetic chain resistance exercises do not affect flexibility of joints negatively, flexibility exercise is not a must in the sessions containing force exercises.

d) Primary Cardio, Secondary Cardio, Primary Force or Secondary Force Exercises are Never Performed after Primary Flexibility.

Primary aim of flexibility (3) exercises is to increase the flexibility of joints. For this aim, they are the exercises performed with plan and knowledge by using FIT principles (frequency, intensity and time). For this reason, there is the rule set as no exercise is performed to reduce the effect or performance of exercise afterwards.

Strategy of exercise (Cardio-Force-Flexibility) which is selected in accordance with the measurement results and the locations of fitness components on the map, prioritizes the improvement of the fitness component in its target. However, when frequency and time factors are considered in and these factors are at their upper limits, the programs in which other fitness components have priority can also be applied alternatively. For instance, even in the situations where cardio strategy is selected with priority, if a person can spare 7 days a week for exercise, sessions from other strategies may also be applied in certain days of a week.

The Rules for Preparing Exercise Session Depending on Frequency and Time in the Cardio Strategy (I.ST):

a. For the selections up to 3 frequencies, Primary Cardio exercises are applied.
b. For the programs with 4-6 frequencies, Secondary Cardio exercises are applied in the sessions which contain Primary Force as these sessions provide priority also to force components.
c. At 1, 2 and 3 frequencies, Force Component is applied as Secondary Force. When 4, 5 and 6 frequencies are reached and Secondary Strategy is included, force component is applied as Primary Force.
d. At the frequencies over 3, the second and the third strategies as well as the first strategies are put into use in the following systematics.
e. In the exercises with 3 frequencies, the first strategy is applied at each of three frequencies, (3×I.ST)
f. In the exercises with 4 frequencies (3×1. ST)+(1×2.ST)
g. In the exercises with 5 frequencies (3×1. ST)+(2×2.ST)
h. In the exercises with 6 frequencies (3×1. ST)+(2×2.ST)+(1×3. ST)
i. In the exercises with 7 frequencies (3×1. ST)+(2×2.ST)+(2×3.ST)

The Rules for Preparing Exercise Session Depending on Frequency and Time in Force Strategy (2.ST):

a) As force component (2) is divided into three sub-groups, (lower extremity (2a), upper extremity (2b), body (2c)) it is included as Primary Force in the programs with 1, 2, 3, 4, 5 and 6 frequencies.
b) In the exercises up to 3 frequencies, as Force Strategy (2. ST) the weakest one in all of the three different areas is assigned as having the first priority, the area of 1st priority is applied first, the area of 2nd priority is applied second and the area of 3rd priority is applied third. (2. ST-a).
c) In the exercises with 4 frequencies, the area of 2nd priority ranks first, the area of 1st priority ranks second and the area of 3rd priority ranks third in addition to 2.ST-a as Force Strategy (2. ST-b).
d) In the exercises with 5 and 6 frequencies, the area of 3rd priority ranks first, the area of 1st priority ranks second and the area of 2nd priority ranks third in addition to 2.ST-a and 2.ST-b as Force Strategy (2.ST-c).
e) In the exercises with 7 frequencies, three strategies (together with a, b, c items of Force Strategy) are put into use together in the following systematics.
f) At the time intervals of 30', 40' and 50' minutes, the other two strategies as well as the Force Strategy in 3 and higher frequencies are put into use in the following systematics.
g) In the exercises with 1 frequency (1×2.ST-a)
h) In the exercises with 2 frequencies (2×2.ST-a)
i) In the exercises with 3 frequencies (2×2.ST-a)+(1×1.ST)
j) In the exercises with 4 frequencies (2×2.ST-a)+(1×2.ST-b)+(1×1.ST)
k) In the exercises with 5 frequencies (1×2.ST-a)+(1×2.ST-b)+(1×2.ST-c)+(2×1.ST)
l) In the exercises with 6 frequencies (2×2.ST-a)+(1×2.ST-b)+(1×2.ST-c)+(2×1.ST)
m) In the exercises with 7 frequencies (2×2.ST-a)+(1×2.ST-b)+(1×2.ST-c)+(2×1.ST)+(1×3.ST)
n) In the exercises of 60', 70', 80 and 90' minutes, however, the 3rd Strategy is utilized only during the session with 7 frequencies since sessions take longer times, and it runs in the following systematics.
o) In the exercises with 1 frequency (1×2.ST-a)
p) In the exercises with 2 frequencies (2×2.ST-a)
q) In the exercises with 3 frequencies (3×2.ST-a)
r) In the exercises with 4 frequencies (2×2.ST-a)+(2×2.ST-b)
s) In the exercises with 5 frequencies (2×2.ST-a)+(2×2.ST-b)+(1×2.ST-c)
t) In the exercises with 6 frequencies (2×2.ST-a)+(2×2.ST-b)+(2×2.ST-c)
u) In the exercises with 7 frequencies (2×2.ST-a)+(2×2.ST-b)+(2×2.ST-c)+(1×3.ST)

The Rules for Preparing Exercise Session Depending on Frequency and Time in Flexibility Strategy (3.ST):

a) Secondary Cardio exercise is not present.
b) At 4 and higher frequencies, the first strategy as well as the third strategy is utilized in the following systematics.
c) At 6 and higher frequencies, the second strategy as well as the third and the first strategies is utilized in the following systematics.
d) In the exercises with 1 frequency (1×3.ST)
e) In the exercises with 2 frequencies (2×3.ST)
f) In the exercises with 3 frequencies (3×3.ST)
g) In the exercises with 4 frequencies (3×3.ST)+(1×1.ST)
h) In the exercises with 5 frequencies (3×3.ST)+(2×1.ST)
1) In the exercises with 6 frequencies (3×3.ST)+(2×1.ST)+(1×2.ST)
j) In the exercises with 7 frequencies (3×3.ST)+(2×1.ST)+(2×2.ST)

The ordering in the Force Strategy is taken as reference in order to appoint the priorities of sub-components in Force Strategies (2.ST) which are applied in the first and third strategies.

I claim:

1. A method for preparing, administering and monitoring a customized exercise strategy and prescription based on data pertaining to a person's health, the method comprising the following steps:

measuring the person's following fitness components:
  a cardiovascular endurance component;
  a muscular strength component;
  a flexibility component; and
  a body composition component;
calculating each of the fitness components as percentage ratios of the person's total fitness score;
calculating weighted percentage ratios and fitness component scores separately for each of the person's fitness component values based on age and gender-related fitness component norms;
calculating a weighted total fitness score based on the scores of all of the fitness components;
generating and displaying a fitness map graphically representing the ratios of said calculated fitness components;
whereby preparing and monitoring the customized exercise strategy comprises, by use of software executed on a suitable system and the fitness map:
  prioritizing the ratios of the health related fitness components in the customized exercise strategy;
  determining an exercise strategy in accordance with measurements of the person's fitness components, the weighted total fitness score and the prioritized health related fitness components;
  dividing said exercise strategy into exercises comprising cardio components, strength components and flexibility components;
  determining a detailed order of exercises for each of the components; and
  preparing a person's customized exercise strategy based on the determined exercise strategy, the person's customized exercise strategy depending on a frequency and time allotted by the person for exercise, and comprising an order of exercises to be performed; and
administering the person's customized exercise strategy.

2. The method of claim 1, further comprising:
re-measuring the person's fitness components; and
administering an updated customized exercise strategy in response to changes in the person's measured fitness components.

3. The method of claim 1, said step of prioritizing comprising prioritizing the ratios of the health related fitness components in the customized exercise strategy as follows:
allocating a largest ratio to exercises relating to the cardiovascular endurance component.

4. The method of claim 3, said step of prioritizing further comprising:
allocating a second largest ratio to exercises relating to the muscular strength component;
a third largest ratio to exercises relating to the body composition component; and
a fourth largest ratio to exercises relating to the muscular flexibility component.

5. The method of claim 1, said step of measuring comprising measuring the person's fitness components by measuring devices.

6. The method of claim 1, wherein each component and fitness exercise is further divided into a primary and secondary component.

7. The method of claim 6, wherein in said step of determining a detailed order of exercises, the detailed order of exercises for each of the components is based on the further primary and secondary components of each of the components.

8. The method of claim 1, wherein:
the method realizes the process steps of calculating the ratios of said calculated fitness components according to age- and gender-related fitness component values and filling the fitness map according to these ratios by software executed on a system;
the sum of the measured fitness components is determined to be 100%, of which a share of percentage is given to each fitness component in terms of the importance of their effect to health, based on the norms set for age and gender;
allocating a largest share of percentage of the mentioned in the fitness map to cardiovascular endurance at 40%, a second largest share of percentage to muscular strength at 35%, a third largest share of percentage to body composition at 15% and a fourth largest share of percentage to flexibility at 10%;
calculating a component score of each component and determining an occupancy ratio of each component in the space allocated to it in the map;
displaying said fitness component levels in the map in accordance with said occupancy ratios; and
obtaining the total fitness score based on all of the fitness component scores of a person.

9. The method of claim 1, wherein said muscular strength component is divided into lower body, upper body and trunk components.

10. The method of claim 7, wherein the step of determining exercise strategy depending on the frequency and time of exercise for each exercise session comprises the steps of:
in each exercise session, determining the rules of exercise depending on the time and frequency allotted per session for each fitness component; and
designating and applying primary and secondary degrees in order to put forth a difference of scope and intensity of each component except the body composition component.

11. A method of graphically displaying a person's fitness components and preparing and administering a customized exercise strategy, the method comprising:
measuring the person's following fitness components:
  a cardiovascular endurance component;
  a muscular strength component;
  a flexibility component; and
  a body composition component;
calculating a score for each of the measured fitness components based on norms related to an age and a gender of the person;
generating and displaying a pie chart wherein the pie chart is allocated into sections for at least cardiovascular endurance, muscular strength, flexibility and body composition;
weighting the calculated scores for each of the measured fitness components based on a respective allocation within the pie chart;
populating the pie chart with the weighted calculated scores;
whereby preparing and monitoring the customized exercise strategy comprises, by use of software executed on a suitable system:
  prioritizing ratios of the fitness components in the customized exercise strategy;
  determining an exercise strategy in accordance with at least the measurements of the person's fitness components and the prioritized health related fitness components;

dividing said exercise strategy into exercises comprising cardio components, strength components and flexibility components;

determining a detailed order of exercises for each of the fitness components; and preparing a person's customized exercise strategy based on the determined exercise strategy, the person's customized exercise strategy depending on a frequency and time allotted by the person for exercise, and comprising an order of exercises to be performed; and administering the person's customized exercise strategy.

12. The method of claim 11, further comprising:

re-measuring the person's fitness components; and administering an updated customized exercise strategy in response to changes in the person's measured fitness components.

13. The method of claim 11, wherein said step of generating comprises:

allocating a largest portion of the pie chart to cardiovascular endurance.

14. The method of claim 13, said step of generating further comprising:

allocating a second largest portion to muscular strength;

allocating a third largest ratio to body composition; and allocating a fourth largest ratio to flexibility.

15. The method of claim 11, wherein the portion of the pie chart allocated to muscular fitness comprises:

a first portion allocated to lower body strength;

a second portion allocated to upper body strength; and a third portion allocated to trunk strength.

16. The method of claim 11, wherein the calculated scores for each of the measured fitness components is on a scale of 0 to 100, and wherein said step of weighting comprises:

multiplying the calculated score for a particular measured fitness component by the percentage allocation for that fitness component, a resulting figure constituting a component-specific percentage of the entire pie chart.

17. The method of claim 16, said step of populating comprising:

filling in the component-specific percentage within the portion of the pie chart allocated for the particular fitness component.

18. The method of claim 16, further comprising:

calculating a total fitness score based on the total of the multiplied calculated scores of all measured fitness components.

19. The method of claim 18, wherein said step of determining an exercise strategy comprises:

determining an exercise strategy in accordance with measurements of the person's fitness components, the weighted total fitness score and the priority of the health related fitness components.

20. The method of claim 11, said cardiovascular endurance component being based on a measurement of maxVO2.

* * * * *